United States Patent
Horii et al.

(10) Patent No.: US 10,473,652 B2
(45) Date of Patent: Nov. 12, 2019

(54) METHOD OF DETECTING TEST SUBSTANCE, SAMPLE ANALYSIS CARTRIDGE, AND SAMPLE ANALYZER

(71) Applicant: SYSMEX CORPORATION, Kobe-shi, Hyogo (JP)

(72) Inventors: Kazuyoshi Horii, Kobe (JP); Tomoyuki Nose, Kobe (JP); Takao Fujiwara, Kobe (JP); Tatsuya Kosako, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 401 days.

(21) Appl. No.: 15/081,070

(22) Filed: Mar. 25, 2016

(65) Prior Publication Data

US 2016/0320375 A1   Nov. 3, 2016

(30) Foreign Application Priority Data

Apr. 30, 2015  (JP) ................. 2015-093387

(51) Int. Cl.
*B01L 3/00* (2006.01)
*G01N 33/543* (2006.01)
(Continued)

(52) U.S. Cl.
CPC ..... *G01N 33/54326* (2013.01); *B01F 5/0647* (2013.01); *B01F 5/0655* (2013.01);
(Continued)

(58) Field of Classification Search
CPC ............. B01F 11/0071; B01F 11/0082; B01F 13/0818; B01F 5/0647; B01F 5/0655;
(Continued)

(56) References Cited

U.S. PATENT DOCUMENTS 5,702,950 A * 12/1997 Tajima .................. B01L 3/021
                                                          210/222
7,708,881 B2  5/2010 Yu
(Continued)

FOREIGN PATENT DOCUMENTS

JP     S52-78493 A    7/1977
JP     H08-62224 A    3/1996
(Continued)

*Primary Examiner* — Maureen Wallenhorst
(74) *Attorney, Agent, or Firm* — Metrolex IP Law Group, PLLC

(57) ABSTRACT

In a method of detecting a test substance, a test substance is detected using a sample analysis cartridge supplied with a sample. The sample analysis cartridge includes: a passage part having a gas-phase space; and liquid containers communicating with the passage part through openings. The liquid containers include: a first liquid container containing a first liquid containing magnetic particles; and a second liquid container containing a second liquid containing a labeled substance. The magnetic particles are sequentially transported to the liquid containers through the gas-phase space in the passage part. Thus, the magnetic particles carry a complex of the test substance and the labeled substance. The test substance is detected based on the labeled substance in the complex.

11 Claims, 21 Drawing Sheets

(51) Int. Cl.
*G01N 33/48* (2006.01)
*B01F 5/06* (2006.01)
*B01F 11/00* (2006.01)
*B01F 13/08* (2006.01)

(52) U.S. Cl.
CPC ...... *B01F 11/0071* (2013.01); *B01F 11/0082* (2013.01); *B01F 13/0818* (2013.01); *B01L 3/50273* (2013.01); *B01L 3/502761* (2013.01); *G01N 33/54306* (2013.01); *G01N 33/54366* (2013.01); *B01L 3/502715* (2013.01); *B01L 2200/0668* (2013.01); *B01L 2200/0673* (2013.01); *B01L 2300/0627* (2013.01); *B01L 2300/087* (2013.01); *B01L 2300/0816* (2013.01); *B01L 2300/0874* (2013.01); *B01L 2300/0877* (2013.01); *B01L 2300/0883* (2013.01); *B01L 2400/043* (2013.01); *G01N 33/48* (2013.01)

(58) Field of Classification Search
CPC ..... B01L 2200/0668; B01L 2200/0673; B01L 2300/0627; B01L 2300/0816; B01L 2300/087; B01L 2300/0874; B01L 2300/0877; B01L 2300/0883; B01L 2400/043; B01L 3/502715; B01L 3/50273; B01L 3/502761; G01N 33/54306; G01N 33/54326; G01N 33/54366; G01N 33/48
USPC .......... 436/63, 149, 150, 174, 180, 526; 422/68.1, 502, 503, 507; 435/7.1, 7.5, 435/29, 39, 287.2, 287.3
See application file for complete search history.

(56) References Cited

U.S. PATENT DOCUMENTS

| | | | |
|---|---|---|---|
| 9,752,989 B2* | 9/2017 | Horii | B01L 3/50273 |
| 2008/0031787 A1 | 2/2008 | Yu | |
| 2009/0227044 A1* | 9/2009 | Dosev | G01N 33/54333 436/526 |
| 2013/0206701 A1 | 8/2013 | Strohmeier et al. | |
| 2015/0093815 A1 | 4/2015 | Kiani et al. | |
| 2018/0003704 A1* | 1/2018 | Horii | G01N 35/00069 |

FOREIGN PATENT DOCUMENTS

| | | |
|---|---|---|
| JP | H08-240596 A | 9/1996 |
| JP | 2009-148735 A | 7/2009 |
| JP | 2015-040804 A | 3/2015 |
| WO | 2012-041809 A1 | 4/2012 |

* cited by examiner

METHOD OF DETECTING TEST SUBSTANCE, SAMPLE ANALYSIS CARTRIDGE, AND SAMPLE ANALYZER

CROSS REFERENCE TO RELATED APPLICATIONS

This application claims priority to prior Japanese Patent Application No. 2015-093387 filed on Apr. 30, 2015 entitled "METHOD OF DETECTING TEST SUBSTANCE, SAMPLE ANALYSIS CARTRIDGE, AND SAMPLE ANALYZER" the entire contents of which are hereby incorporated by reference.

BACKGROUND

There is a technology to perform sample analysis by a sample analyzer using a cartridge-type fluid device (see, for example, U.S. Pat. No. 7,708,881: Patent Document 1).

Patent Document 1 discloses a technology to analyze a sample using a fluid device including liquid containers containing a liquid and microchannels connecting the liquid containers. A test substance is carried by magnetic particles, which are carriers, and transported by magnetic force. The magnetic particles carrying the test substance are transported between the liquid containers adjacent to each other through the microchannel by the magnetic force. The liquid contained in the liquid containers is supplied to each liquid container through the microchannels.

SUMMARY

A method of detecting a test substance according to a first embodiment is a method of detecting a test substance contained in a sample by use of a sample analysis cartridge supplied with the sample, the sample analysis cartridge including a passage part with a gas-phase space and liquid containers disposed along the passage part and communicating with the passage part through openings, the liquid containers including a first liquid container containing a first liquid containing magnetic particles for carrying the test substance, and a second liquid container containing a second liquid containing a labeled substance that can be coupled to the test substance, the method comprising: sequentially transporting the magnetic particles to the liquid containers through the gas-phase space in the passage part, and thus allowing the magnetic particles to carry a complex of the test substance and the labeled substance and detecting the test substance based on the labeled substance in the complex.

A sample analysis cartridge according to a second embodiment is a sample analysis cartridge set in a sample analyzer and supplied with a sample for detecting a test substance contained in the sample, comprising: a passage part with a gas-phase space; and liquid containers disposed along the passage part and communicating with the passage part through openings, wherein the liquid containers include a first liquid container containing a first liquid containing magnetic particles that carries the test substance, and a second liquid container containing a second liquid containing a labeled substance that can be coupled to the test substance, and the liquid containers are arranged such that the magnetic particles are sequentially transported to the liquid containers through the gas-phase space in the passage part, and thus a complex of the test substance and the labeled substance is carried by the magnetic particles.

A sample analyzer according to a third aspect of the embodiment is a sample analyzer which analyzes a test substance contained in a sample supplied to a sample analysis cartridge, comprising: a setting part that sets a sample analysis cartridge including a passage part with a gas-phase space, and liquid containers disposed along the passage part and communicating with the passage part through openings, the liquid containers including a first liquid container containing a first liquid containing magnetic particles that carries the test substance, and a second liquid container containing a second liquid containing a labeled substance that can be coupled to the test substance; a magnetic source that generates magnetic force acting on the magnetic particles in the sample analysis cartridge set in the setting part, thereby transporting the magnetic particles between the liquid containers; and a detector that detects the test substance based on the labeled substance in a complex of the test substance and the labeled substance carried by the magnetic particles, wherein the magnetic source moves near the sample analysis cartridge set in the setting part, thereby sequentially transporting the magnetic particles to the liquid containers through the gas-phase space in the passage part.

In sample measurement using the sample analysis cartridge, it is possible to suppress the mixing of a liquid in a liquid container into a liquid in a liquid container adjacent thereto by movement of magnetic particles.

EMBODIMENTS

With reference to the drawings, embodiments are described below.

(Overview of Method of Detecting Test Substance)

Figure 1:
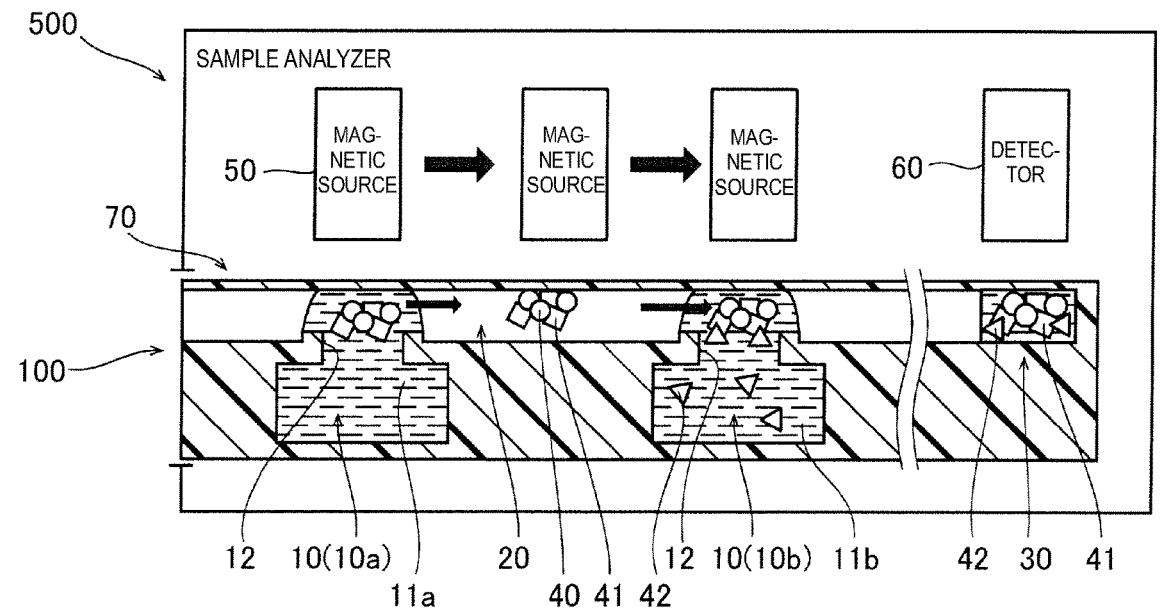
FIG. 1 is a diagram for explaining an overview of a method of detecting a test substance.

With reference to FIG. 1, description is given of an overview of a method of detecting a test substance according to this embodiment.

The method of detecting a test substance according to this embodiment is a method of detecting a test substance contained in a sample by use of a sample analysis cartridge supplied with the sample. Sample analysis cartridge 100 is capable of receiving a sample, and is inserted into sample analyzer 500 to enable sample analyzer 500 to analyze the sample. A sample such as tissues obtained from a patient or a body fluid and a blood obtained from the patient is injected into sample analysis cartridge 100. The cartridge having the sample injected therein is set in setting part 70 in sample analyzer 500. The sample injected into sample analysis cartridge 100 is analyzed by a predetermined assay based on functions of the cartridge and functions of the analyzer.

Sample analysis cartridge 100 includes passage part 20 having a gas-phase space, liquid containers 10 disposed along passage part 20 and communicating with passage part 20 through openings 12, and detection tank 30 for detecting test substance 41.

Liquid containers 10 include: first liquid container 10a containing first liquid 11a containing magnetic particles 40 for carrying test substance 41; and second liquid container 10b containing second liquid 11b containing labeled substance 42 that can be coupled to test substance 41. Liquid containers 10 may further include a liquid container containing another liquid.

The level of the liquid contained in each of liquid containers 10 is not particularly limited as long as the container contains an amount of liquid required for detection and there is the gas-phase space in passage part 20. For example, FIG. 1 illustrates an example where the levels of the liquids contained in liquid containers 10 are higher than the openings of the liquid containers. Therefore, in FIG. 1, the liquids contained in liquid containers 10 are also in passage part 20 above openings 12. Here, the gas-phase space means a space filled with gas, through which magnetic particles 40 invariably pass when magnetic particles 40 are transported from the liquid in one of liquid containers 10 to the liquid in liquid container 10 adjacent thereto. Note that the inside of passage part 20 may be entirely set as the gas-phase space or may be partially set as the gas-phase space. To be more specific, a part of a transportation path of magnetic particles 40 in passage part 20 between two adjacent liquid containers 10 may be set as the gas-phase space. Note that, as for the gas, air is preferably used, but nitrogen or the like can also be used. Moreover, FIG. 1 illustrates an example where the opening area of each of openings 12 is smaller than the area of the bottom inner surface of each of liquid containers 10.

Liquid containers 10 may be configured in an empty state of containing no liquids therein, respectively, as an initial state, and also configured to be supplied with the liquids, respectively, upon usage of sample analysis cartridge 100. More specifically, there is a separate liquid chamber storing a liquid aside from liquid containers 10, and the liquids may be supplied to liquid containers 10 from the liquid chamber upon usage. Alternatively, sample analyzer 500 may be configured, for example, to store liquids and inject the liquids into liquid containers 10 upon usage.

The gas-phase space is provided in passage part 20. A gas-liquid interface is formed between the liquids in liquid containers 10 and the gas-phase space.

In sample analysis cartridge 100, test substance 41 is carried by magnetic particles 40 and transported to respective liquid containers 10 together with magnetic particles 40. Magnetic particles 40 are transported passing through the gas-phase space in passage part 20. Magnetic particles 40 are transported by magnetic force between adjacent liquid containers 10. The transportation of magnetic particles 40 by the magnetic force is performed using magnetic source 50 in sample analyzer 500.

With such a configuration, in the method of detecting a test substance according to this embodiment, magnetic particles 40 for carrying test substance 41 are sequentially transported to the liquid containers 10, thereby allowing magnetic particles 40 to carry a complex of test substance 41 and labeled substance 42. Magnetic particles 40 are transported through the gas-phase space in passage part 20 between adjacent liquid containers 10. During the transportation process of magnetic particles 40, test substance 41 is carried by magnetic particles 40 in first liquid container 10a, and labeled substance 42 is coupled to test substance 41 in second liquid container 10b. Next, in this embodiment, test substance 41 is detected based on labeled substance 42 in the complex. Magnetic particles 40 carrying the complex are transported to detection tank 30. In detection tank 30, labeled substance 42 and a substrate react with each other. In detection tank 30, test substance 41 is detected by detector 60 in sample analyzer 500 based on labeled substance 42.

Magnetic source 50 is, for example, a permanent magnet or an electromagnet. Magnetic source 50 generates magnetic force acting on magnetic particles 40 in sample analysis cartridge 100 set in setting part 70, thereby transporting magnetic particles 40 between liquid containers 10. For example, magnetic source 50 itself moves to transport magnetic particles 40. More than one magnetic source 50 may be disposed along the transportation path of magnetic particles 40, and magnetic sources 50 generating the magnetic force may be switched to transport magnetic particles 40. In the example of FIG. 1, magnetic source 50 moves near sample analysis cartridge 100 set in setting part 70, thereby sequentially transporting magnetic particles 40 to liquid containers 10 through the gas-phase space in passage part 20.

During the transportation of magnetic particles 40, magnetic particles 40 move into the gas-phase space in passage part 20 by breaking through the gas-liquid interface from inside the liquid in the liquid container 10, and then move into the liquid in adjacent liquid container 10 by breaking through the gas-liquid interface from the gas-phase space. Thus, the mixing of the liquids in respective liquid containers 10 is suppressed during the transportation of magnetic particles 40 between adjacent liquid containers 10. During the transportation of magnetic particles 40, the liquids in respective liquid containers 10 may leak into passage part 20 from openings 12 as long as the amount of the liquid leaking into passage part 20 is not as large as that is mixed with the liquid in another liquid container 10 and the gas-phase space remains in passage part 20. Even in such a case, magnetic particles 40 can move through the gas-phase space in passage part 20. Thus, it is possible to suppress the mixing of the liquid in liquid container 10 into the liquid in liquid container 10 adjacent thereto by the movement of magnetic particles 40.

As described above, in the method of detecting a test substance according to this embodiment, it is possible to suppress the mixing of the liquid in liquid container 10 into the liquid in liquid container 10 adjacent thereto by the movement of magnetic particles 40 in sample analysis using sample analysis cartridge 100.

Figure 2:
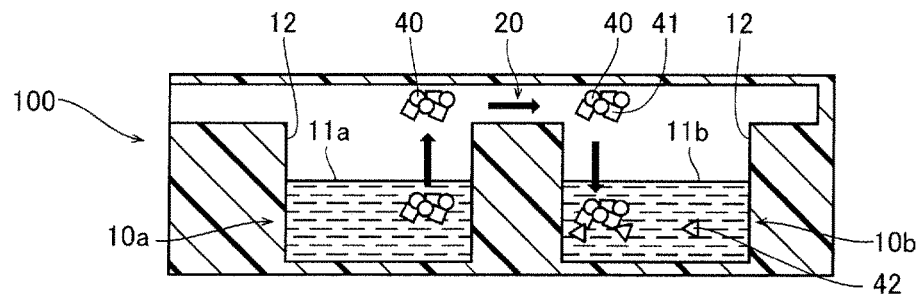
FIG. 2 is a diagram illustrating another configuration example of liquid containers and a passage part.

FIG. 2 is a diagram illustrating another configuration example of liquid containers 10 and passage part 20.

In the configuration example of FIG. 2, the levels of the liquids contained in liquid containers 10 are set lower than openings 12. In this case, magnetic particles 40 are pulled up to the gas-phase space in passage part 20 from inside the liquid 11a in first liquid container 10a, and then transported to second liquid container 10b. FIG. 2 also illustrates an example where the opening area of the openings 12 is set larger than that of openings 12 illustrated in FIG. 1.

In the configuration examples of FIGS. 1 and 2, passage part 20 is disposed above respective liquid containers 10. To be more specific, passage part 20 is disposed close to the upper surface of sample analysis cartridge 100, and openings 12 are formed in upper parts of liquid containers 10. Therefore, the gas-phase space in passage part 20, through which magnetic particles 40 are transported, can be easily provided. In this case, magnetic source 50 in sample analyzer 500 outside sample analysis cartridge 100 can be set close to passage part 20. As a result, stronger magnetic force can be generated to act on magnetic particles 40. Thus, magnetic particles 40 can be efficiently transported. Moreover, just by disposing magnetic source 50 close to passage part 20, magnetic particles 40 can be easily allowed to pass through openings 12.

Moreover, in the configuration examples of FIGS. 1 and 2, magnetic particles 40 are transported by moving magnetic source 50 along passage part 20 above sample analysis cartridge 100. In this case, magnetic particles 40 can be transported while allowing stronger magnetic force to act on magnetic particles 40 by disposing magnetic source 50 close to passage part 20. As a result, magnetic particles 40 can be easily transported so as to pass through the gas-phase space in passage part 20.

(Overview of Sample Analyzer)

Figure 3:
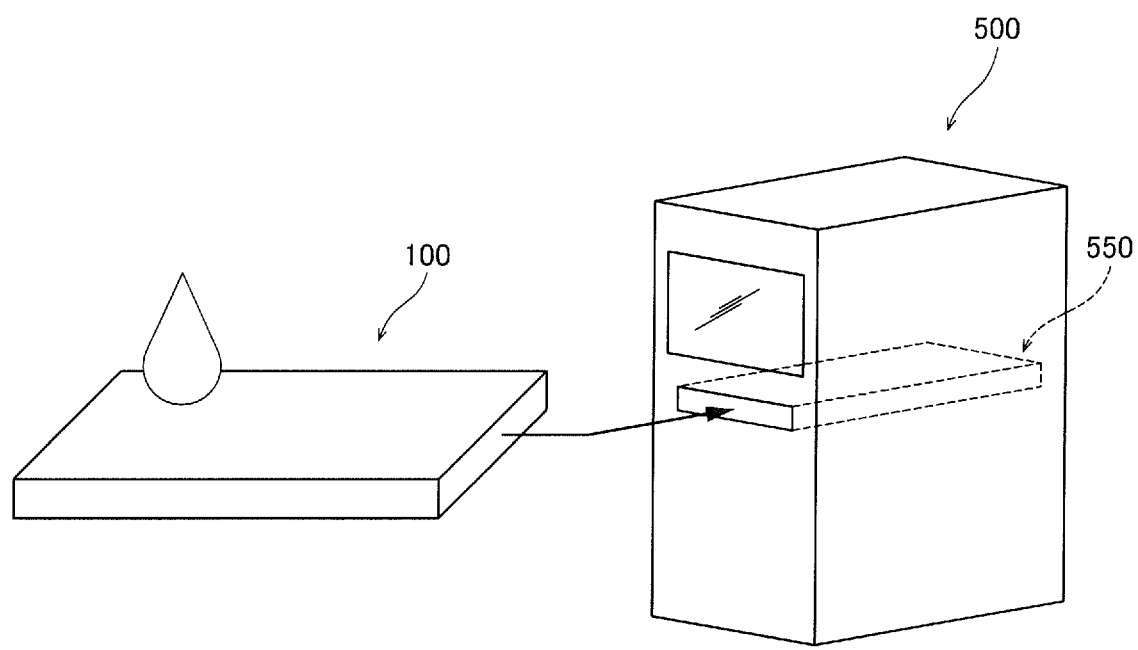
FIG. 3 is a schematic view for explaining an overview of a sample analyzer.

FIG. 3 illustrates an overview of sample analyzer 500 according to this embodiment. Sample analyzer 500 can determine whether or not there is a test substance in a sample and can also determine the concentration of the test substance in the sample. Sample analyzer 500 is small and has a size that can be installed on a desk in an examination room where a doctor examines a patient, for example. In this embodiment, the size of sample analyzer 500 is, for example, about 150 cm$^2$ to 300 cm$^2$ in installation area. Sample analyzer 500 has a slot into which sample analysis cartridge 100 is inserted, for example. Sample analysis cartridge 100 inserted into the slot is set in setting part 550 in the sample analyzer. Sample analyzer 500 performs analysis processing on sample analysis cartridge 100 set in setting part 550.

(Configuration Example of Sample Analysis Cartridge)

Figure 4:
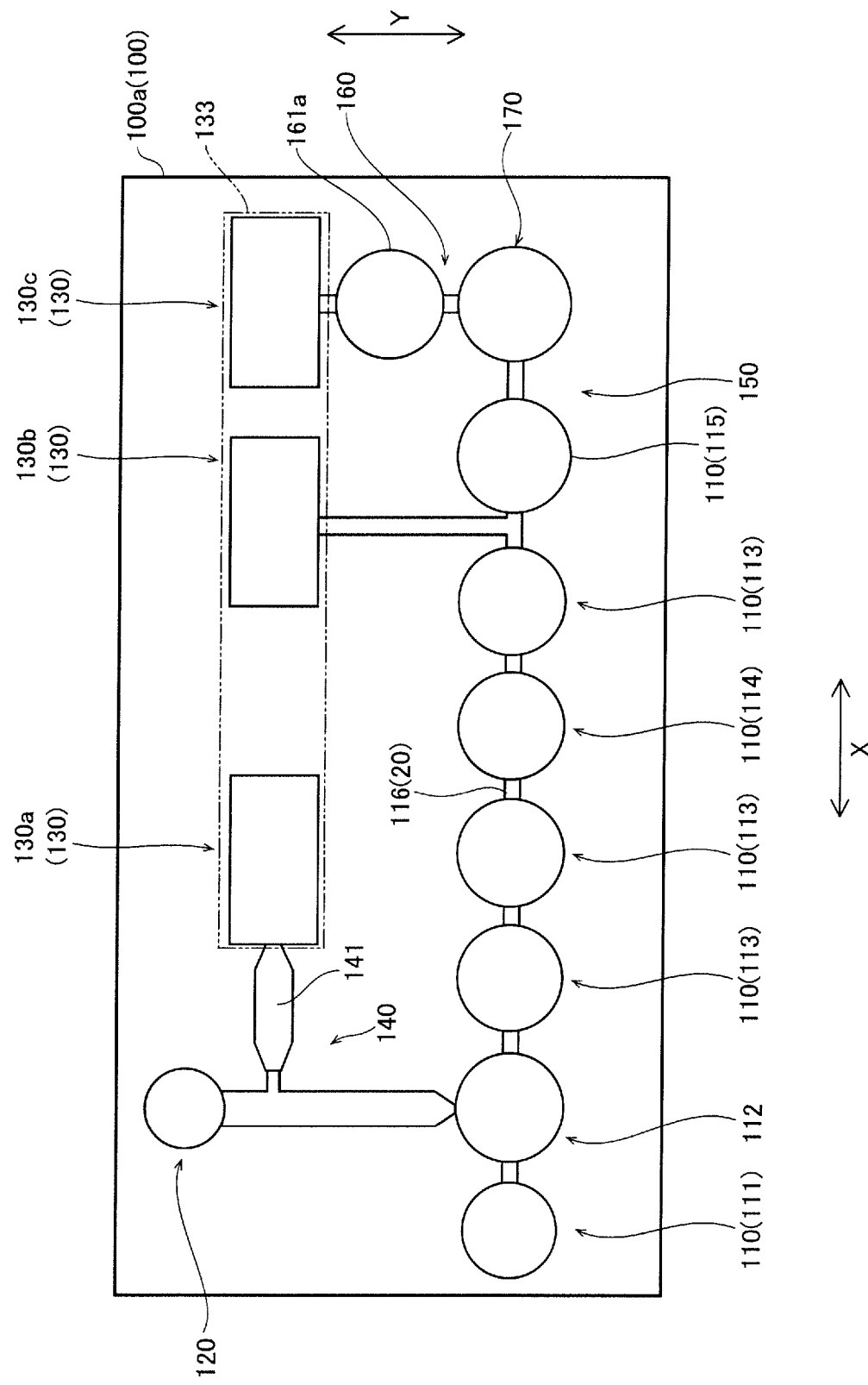
FIG. 4 is a plan view illustrating a configuration example of a sample analysis cartridge.

FIG. 4 illustrates a specific configuration example of sample analysis cartridge 100 according to this embodiment. Sample analysis cartridge 100 may be a disposable cartridge. In such a case, sample analysis cartridge 100 is stored in a state of being housed in a package, and is taken out of the package for use.

Sample analysis cartridge 100 includes liquid containers 110 containing liquids such as a sample, a reagent and a cleaning liquid. Some reagents contain magnetic particles, which react with a substance containing a test substance. Sample analysis cartridge 100 includes detection tank 170 and liquid reaction part 112.

In this embodiment, liquid containers 110 include first liquid container 111, third liquid container 113, second liquid container 114, and fourth liquid container 115. First liquid container 111, third liquid container 113, second liquid container 114, and fourth liquid container 115 as well as liquid reaction part 112 are arranged along passage part 116 with a gas-phase space. The magnetic particles are transported between respective liquid containers 110 through the gas-phase space in passage part 116.

The sample is injected into blood cell separator 120 in sample analysis cartridge 100. Sample analysis cartridge 100 having blood cell separator 120 sealed therein is inserted into sample analyzer 500.

Sample analysis cartridge 100 has air chamber 130. Air sent from air chamber 130 transports some of the liquids in sample analysis cartridge 100.

(Configuration Example of Sample Analyzer)

Figure 5:
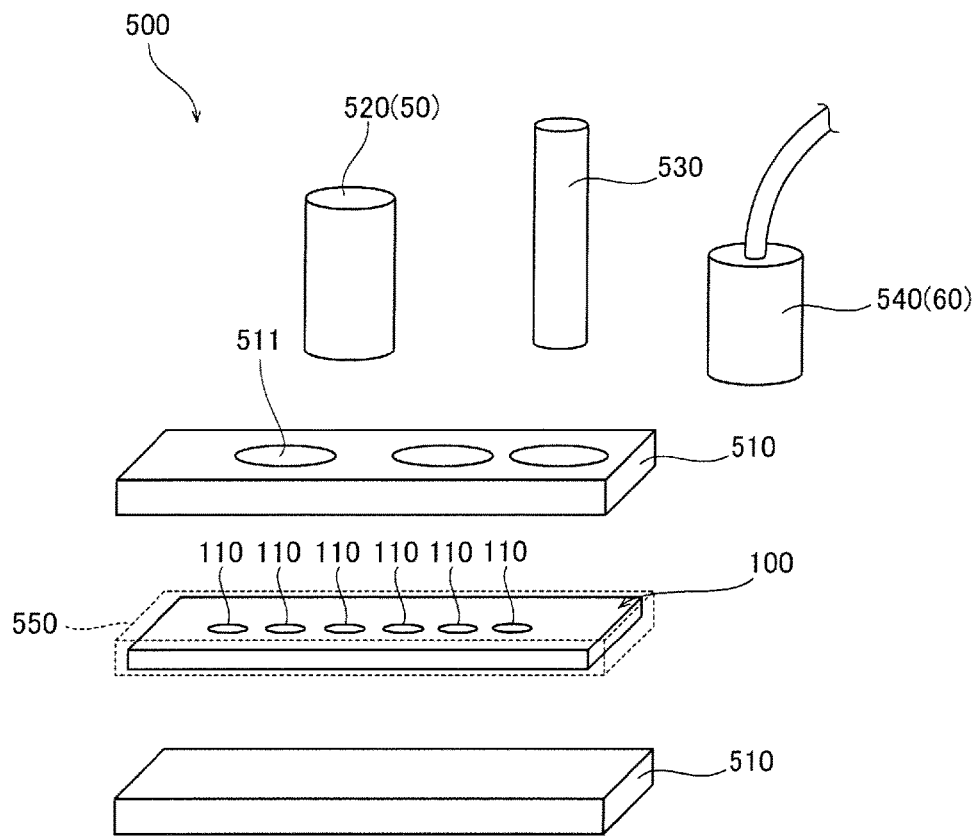
FIG. 5 is a schematic view illustrating a configuration example of the sample analyzer.

FIG. 5 illustrates a configuration example of sample analyzer 500. Sample analyzer 500 includes heat blocks 510, permanent magnet 520, plunger 530, detector 540, and setting part 550. Setting part 550 holds sample analysis cartridge 100. Setting part 550 may have any structure that can hold sample analysis cartridge 100.

Heat blocks 510 adjust the temperature of sample analysis cartridge 100 inserted into sample analyzer 500. Heat blocks 510 may be disposed so as to come into contact with the upper and lower surfaces of sample analysis cartridge 100. Heat blocks 510 may include a part of or all of setting part 550.

In sample analyzer 500, magnetic particles contained in some of the liquid containers in sample analysis cartridge 100 are transported by magnetic force of permanent magnet 520. As for magnetic source 50 in sample analyzer 500, an electromagnet other than permanent magnet 520 may be used.

In sample analyzer 500, plunger 530 pushes down air chamber 130 in sample analysis cartridge 100. Air chamber 130 is pushed down by plunger 530 to send air, thereby transporting some of the liquids in sample analysis cartridge 100. Sample analyzer 500 can control the amount of air sent from air chamber 130 by adjusting how much the air chamber is pushed down by plunger 530. Sample analyzer 500 can adjust the amount of the liquids to be transported, by controlling the air amount. Sample analyzer 500 can apply a negative pressure to sample analysis cartridge 100 by returning plunger 530 that is pushed down. Sample analyzer 500 can transport the transported liquid in an opposite direction by the negative pressure. Some of the liquids in sample analysis cartridge 100 are moved back and forth in a flow path inside sample analysis cartridge 100 by the vertical movement of plunger 530.

Heat block 510 has holes 511 for permanent magnet 520 and plunger 530 to access sample analysis cartridge 100. Holes 511 are provided in heat block 510 disposed on the upper surface of sample analysis cartridge 100, for example. When permanent magnet 520 and plunger 530 access sample analysis cartridge 100 from both directions, holes may be provided in both of heat blocks 510 on the upper and lower surfaces of sample analysis cartridge 100. Some of holes 511 provided in heat block 510 may be recesses or grooves that do not penetrate heat block 510.

Detector 540 may be a light detector configured to detect light generated by reaction between a reagent and a complex containing a test substance. Detector 540 is, for example, a photomultiplier tube.

(Explanation of Assay)

Figure 6:
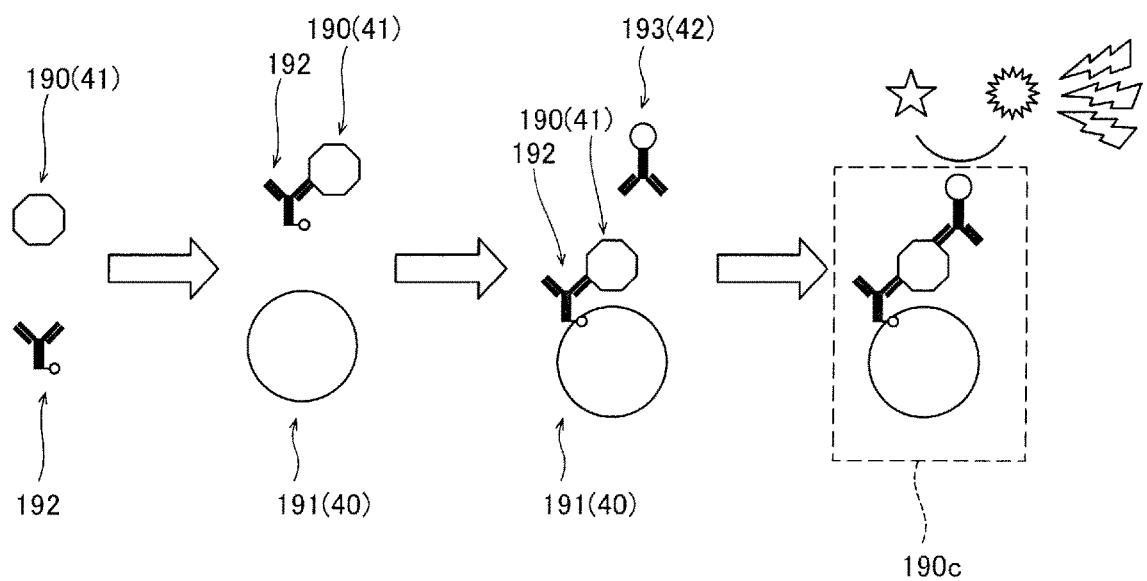
FIG. 6 is a diagram for explaining an example of assay.

With reference to FIG. 6, an overview of assay (analysis method) is described.

Test substance 190 includes, for example, an antigen. As an example, in FIG. 6, the antigen is a hepatitis B surface antigen. The test substance may be an antigen, an antibody, or one or more of other proteins.

An R1 reagent contains capture substance 192 to be coupled to test substance 190. Capture substance 192 includes, for example, an antibody to be coupled to test substance 190. In the example of FIG. 6, the antibody is a biotin-coupled HBs monoclonal antibody.

Test substance 190 coupled to the R1 reagent is coupled to magnetic particle 191. Magnetic particle 191 is contained in an R2 reagent. Magnetic particle 191 serves as a carrier of the test substance. In the example of FIG. 6, magnetic particle 191 is, for example, a streptavidin-coupled magnetic particle having its surface coated with avidin. The avidin of magnetic particle 191 is likely to be coupled to the biotin of the R1 reagent. Thus, connectivity between magnetic particle 191 and capture substance 192 in the R1 reagent is improved.

The coupled body of test substance 190, capture substance 192, and magnetic particle 191 is separated from an unreacted substance by cleaning with a cleaning liquid. After the cleaning, the coupled body of test substance 190, capture substance 192, and magnetic particle 191 reacts with labeled substance 193 contained in an R3 reagent.

Labeled substance 193 includes, for example, a labeled antibody. In the example of FIG. 6, the labeled antibody is an ALP labeled HBsAg monoclonal antibody. Note that, in the case of the example of FIG. 6, labeled substance 193 is coupled to test substance 190 in the coupled body of test substance 190, capture substance 192, and magnetic particle 191. Labeled substance 193 may be coupled to capture substance 192 or may be coupled to magnetic particle 191.

The labeled substance may be an antigen, an antibody, or one or more of other proteins, and is selected according to test substance 190.

Hereinafter, a reactant obtained by reacting at least test substance 190 and magnetic particle 191 with labeled substance 193 is called "complex 190c". Complex 190c may contain capture substance 192 in the R1 reagent.

Complex 190c is separated from the unreacted substance by cleaning with the cleaning liquid. After the cleaning, complex 190c is combined with an R4 reagent. A reactant obtained by reacting complex 190c with the R4 reagent is called a "mixed liquid". The R4 reagent has a composition that facilitates light emission by complex 190c. The R4 reagent is, for example, a buffer liquid.

An R5 reagent is added to the mixed liquid. The R5 reagent includes, for example, a substrate that reacts with complex 190c to facilitate light emission. Complex 190c reacts with the substrate in the R5 reagent. Detector 540 measures emission intensity of light generated by reaction between complex 190c and the R5 reagent.

FIG. 6 illustrates an example of combination where test substance 190 and labeled substance 193 are the antigen and antibody. However, any combination other than the combination of antigen and antibody may also be employed. For example, the following combinations may be used, such as (1) test substance 190 is the antibody and labeled substance 193 is the antigen, (2) test substance 190 is the antibody and labeled substance 193 is the antibody, (3) test substance 190 is the antigen and labeled substance 193 is the antigen, and (4) test substance 190 is the antigen and antibody, and labeled substance 193 is the antigen and antibody.

(Description of Operations According to Embodiment)

Figure 7:
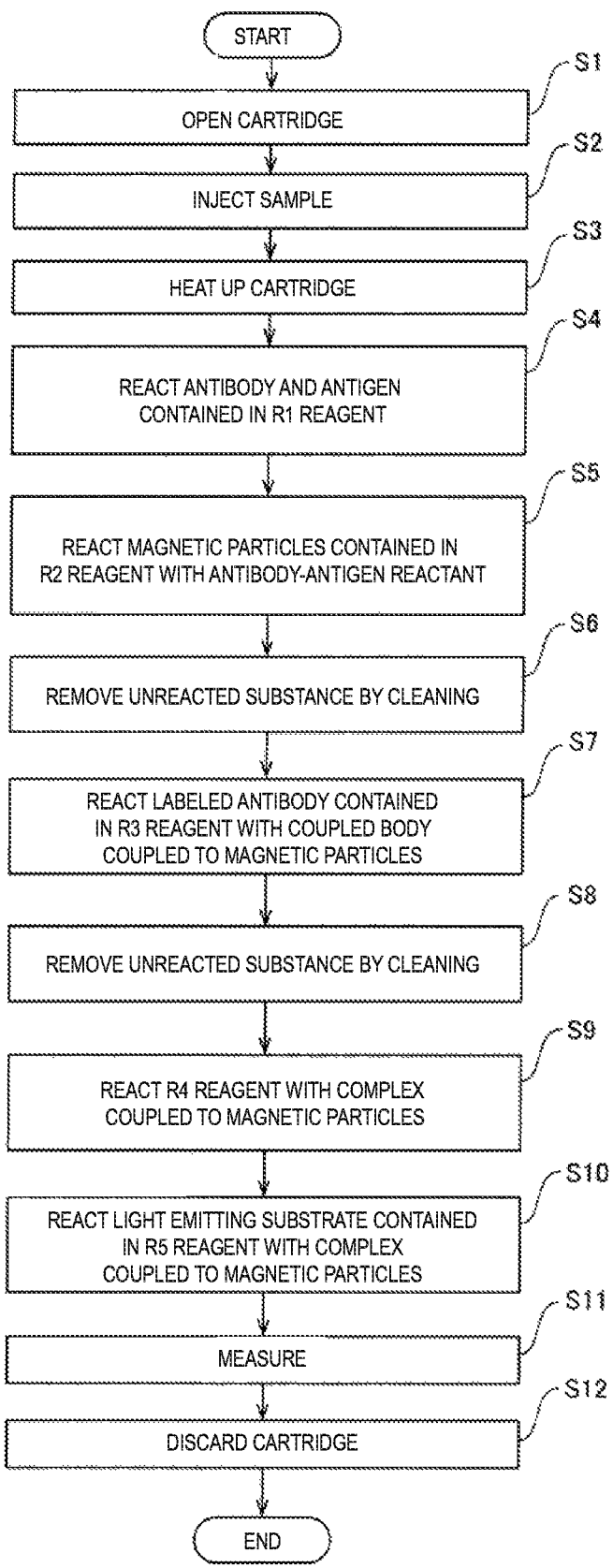
FIG. 7 is a flowchart for explaining a flow of sample analysis.

FIG. 7 illustrates an operation example when the above assay is performed using sample analyzer 500 and sample analysis cartridge 100 according to this embodiment. In the description of the operations, FIG. 4 is referred to for the configuration of sample analysis cartridge 100, and FIG. 5 is referred to for sample analyzer 500.

In Step S1, sample analysis cartridge 100 is opened from a package.

In Step S2, a sample obtained from a patient is injected into blood cell separator 120 in the opened sample analysis cartridge 100. After the injection of the sample, sample analysis cartridge 100 is inserted into sample analyzer 500 and then set in setting part 550. The sample injected into sample analysis cartridge 100 flows through sample flow path 140 in sample analysis cartridge 100.

In Step S3, heat blocks 510 adjusts the temperature of the inserted sample analysis cartridge 100. For example, heat blocks 510 heat up sample analysis cartridge 100.

In Step S4, sample analyzer 500 reacts the antibody contained in the R1 reagent with the antigen that is test substance 190. Sample analyzer 500 uses plunger 530 to push down air chamber 130a. The R1 reagent is pushed out to sample flow path 140, through which test substance 190 flows, by the air sent from air chamber 130a.

Sample analyzer 500 moves up and down plunger 530. The mixed liquid of the sample and the R1 reagent is moved back and forth within the sample flow path 140 by a negative pressure and a positive pressure, which are alternately generated according to the up-and-down movement of plunger 530. The mixed liquid is agitated by being moved back and forth within sample flow path 140. Thus, the reaction between the sample and the R1 reagent is facilitated. As a result of the reaction, an antigen-antibody reactant is generated in the mixed liquid of the sample and the R1 reagent. Sample analyzer 500 further pushes down plunger 530 to push out the mixed liquid of the sample and the R1 reagent to liquid reaction part 112.

In Step S5, sample analyzer 500 reacts magnetic particle 191 contained in the R2 reagent with the antigen-antibody reactant contained in the mixed liquid of the sample and the R1 reagent. Sample analyzer 500 uses the magnetic force of permanent magnet 520 to transport magnetic particle 191 from first liquid container 111 to liquid reaction part 112. In liquid reaction part 112, a coupled body of magnetic particle 191 is generated by the reaction between magnetic particle 191 and the antigen-antibody reactant.

In Step S6, sample analyzer 500 uses the magnetic force of permanent magnet 520 to transport the coupled body of magnetic particle 191 to third liquid container 113. Sample analyzer 500 separates the coupled body of magnetic particle 191 from an unreacted substance in third liquid container 113. The unreacted substance is removed by cleaning.

In Step S7, sample analyzer 500 uses the magnetic force of permanent magnet 520 to transport the cleaned coupled body of magnetic particle 191 to second liquid container 114. Sample analyzer 500 reacts the labeled antibody contained in the R3 reagent with the coupled body of magnetic particle 191 in second liquid container 114. Complex 190$c$ is generated by the reaction between the labeled antibody and the coupled body of magnetic particle 191.

In Step S8, sample analyzer 500 uses the magnetic force of permanent magnet 520 to transport complex 190$c$ to third liquid container 113. An unreacted substance is removed by cleaning.

In Step S9, sample analyzer 500 uses the magnetic force of permanent magnet 520 to transport complex 190$c$ to fourth liquid container 115. Complex 190$c$ reacts with the buffer liquid contained in the R4 reagent. In fourth liquid container 115, complex 190$c$ reacts with the buffer liquid contained in the R4 reagent. Sample analyzer 500 uses plunger 530 to push down air chamber 130$b$, and pushes out the mixed liquid of complex 190$c$ and the buffer liquid to detection tank 170 through mixed liquid flow path 150.

In Step S10, the light emitting substrate contained in the R5 reagent is added to the mixed liquid of complex 190$c$ and the buffer liquid. Sample analyzer 500 uses plunger 530 to push down air chamber 130$c$, and pushes out the R5 reagent to detection tank 170 through R5 flow path 160. In detection tank 170, the R5 reagent is added to the mixed liquid of complex 190$c$ and the buffer liquid. The light emitting substrate reacts with complex 190$c$.

In Step S11, detector 540 detects light generated by the reaction between the labeled antibody in complex 190$c$ and the light emitting substrate. Detector 540 measures emission intensity of the light, for example.

In Step S12, sample analysis cartridge 100 is taken out of sample analyzer 500 and discarded upon completion of the measurement. No sample or reagent leaks to the outside from the discarded sample analysis cartridge 100. Thus, biohazard risks can be reduced. Moreover, sample analyzer 500 also generates no waste liquid.

[Configuration of Respective Parts in Sample Analysis Cartridge]

(Configuration of Liquid Container)

Figure 8:
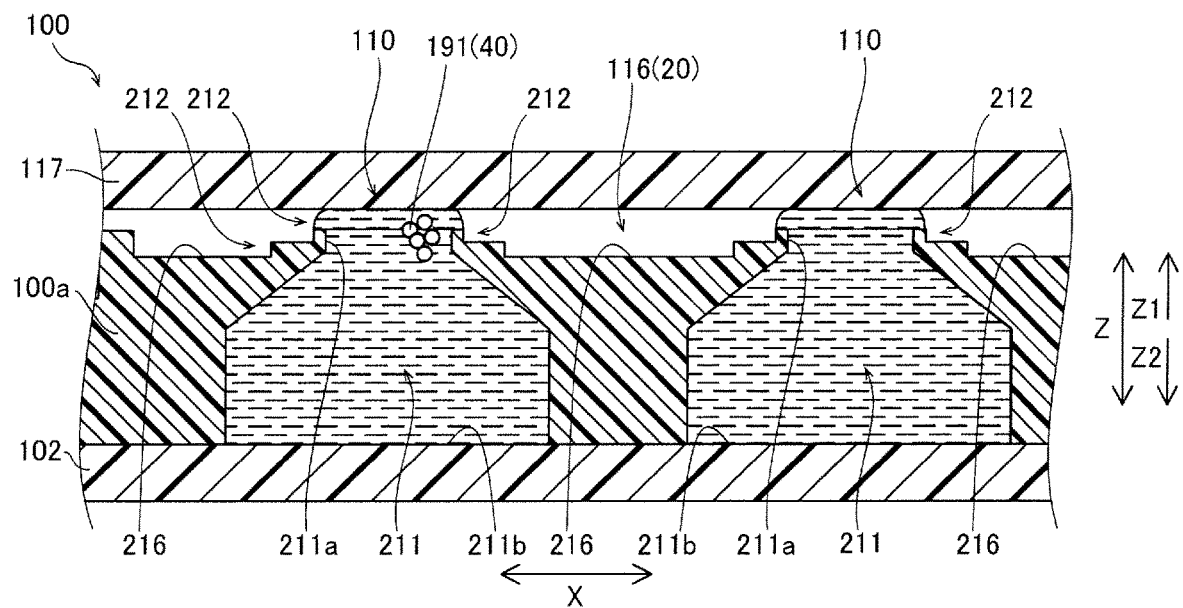
FIG. 8 is a cross-sectional view illustrating a configuration example of the liquid container in the sample analysis cartridge.

FIG. 8 illustrates a configuration example of liquid containers 110 in sample analysis cartridge 100. Liquid containers 110 may be recess parts formed integrally with cartridge main body 100$a$, for example.

Sample analyzer 500 executes the assay by transporting magnetic particles 191 through the gas-phase space in passage part 116 between liquid containers 110. Thus, sample analyzer 500 can execute the assay for analysis while suppressing the mixing of the liquid in liquid container 110 into the liquid in liquid container 110 adjacent thereto by the movement of magnetic particles 191. When the liquid contained in liquid container 110 is mixed into the liquid contained in another liquid container 110 by the movement of magnetic particles 191, reaction conditions change in the liquid in another liquid container 110. Such a change in reaction conditions reduces a reaction effect of the sample and the substance in the reagent. As a result, there may be influence on accuracy and the like of the measurement result obtained by sample analyzer 500. Therefore, the analysis accuracy of sample analyzer 500 is improved by suppressing the mixing of the liquid contained in liquid container 110 into the liquid contained in another liquid container 110.

Moreover, it is no longer required to consider the compatibility between the liquids contained in liquid containers 110 by suppressing the mixing of the liquid contained in liquid container 110 into the liquid contained in another liquid container 110. Thus, the degree of freedom of selection of the liquids contained in liquid containers 110 is increased. As a result, combinations of reagents corresponding to various test items can be contained in liquid containers 110. Since various combinations of reagents can be contained in liquid containers 110, the type of the cartridge can be diversified.

Figure 9:
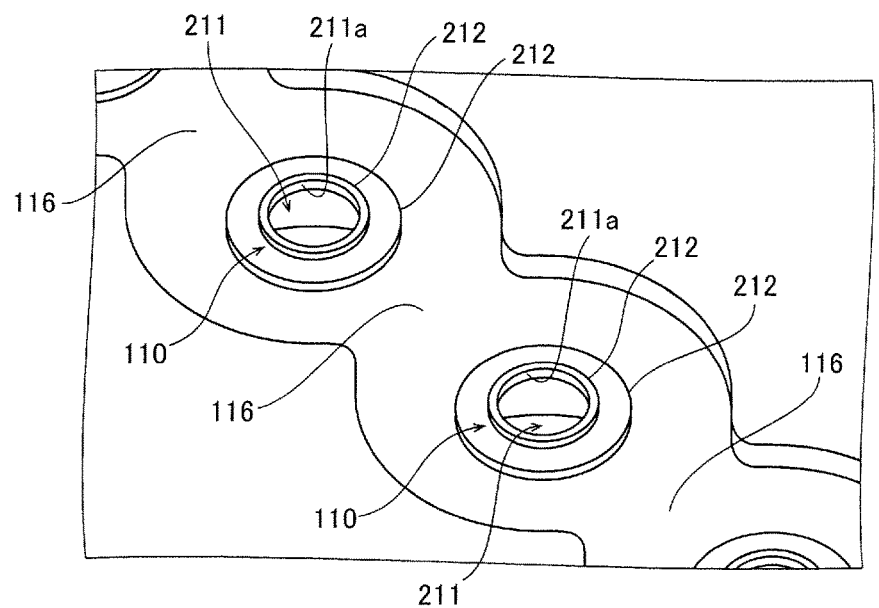
FIG. 9 is a perspective view illustrating a configuration example of the liquid container.

Meanwhile, each of liquid containers 110 has a liquid storage portion communicating with a surface region connected to passage part 116 through opening 211$a$. More specifically, liquid container 110 has opening 211$a$ and recessed liquid storage part 211 communicating with opening 211$a$ and capable of storing a liquid inside. In this embodiment, each of first liquid container 111, third liquid container 113, and second liquid container 114 (see FIG. 4) has opening 211$a$ and liquid storage part 211. Opening 211$a$ is formed in the upper part of liquid container 110. Around opening 211$a$, step part 212 (see FIG. 9) is provided. The liquid contained in liquid container 110 may be not only in liquid storage part 211 but also in passage part 116 above liquid container 110. Moreover, sample analysis cartridge 100 has a Z2-side surface covered with sheet 102

In the configuration example illustrated in FIG. 8, the area of bottom inner surface 211$b$ of liquid storage part 211 is larger than the opening area of opening 211$a$. Therefore, the amount of the liquid that can be contained in liquid storage part 211 can be increased.

Liquid containers 110 in sample analysis cartridge 100 may have a structure to further suppress the mixing of the liquid contained in liquid container 110 into the liquid contained in another liquid container 110 by the movement of magnetic particles 191. For example, as such a structure, grooves 216 may be provided by denting the surface of passage part 116.

The liquids in respective liquid containers 110 may leak into passage part 116 (see FIG. 9) through openings 211$a$ as long as the amount of the liquid leaking into passage part 116 is not as large as that is mixed with the liquid in another liquid container 110 and the gas-phase space remains in passage part 116. In this case, even if the liquid leaks out to passage part 116, magnetic particles 191 are transported to adjacent liquid container 110 through the gas-phase space in passage part 116. Thus, it is possible to suppress the mixing of the liquid contained in liquid container 110 into the liquid contained in another liquid container 110 by the movement of magnetic particles 191. When a structure is provided to further suppress the mixing of the liquid contained in liquid container 110 into the liquid contained in another liquid container 110 by the movement of magnetic particles 191, it is possible to further suppress the mixing of the liquid contained in liquid container 110 into the liquid contained in another liquid container 110 by the movement of magnetic particles 191. For example, when recessed grooves 216 are provided in passage part 116, even if the liquid contained in liquid container 110 is mixed with the liquid contained in another liquid container 110 in the groove, magnetic particles 191 are transported to adjacent liquid container 110 through the gas-phase space in passage part 116. Thus, it is possible to further suppress the mixing of the liquid contained in liquid container 110 into the liquid contained in another liquid container 110 by the movement of magnetic particles 191.

Cover part 117 may be provided on the outer surface side of sample analysis cartridge 100. In the configuration example of FIG. 8, passage part 116 is disposed so as to be exposed to the upper surface of sample analysis cartridge main body 100a, and sample analysis cartridge 100 has cover part 117 covering liquid containers 110 and passage part 116. Cover part 117 is configured to sandwich and hold the liquid between the liquid containers and cover part 117.

In the configuration example of FIG. 8, cover part 117 covers the upper surfaces of liquid containers 110 and passage part 116 from the upper surface side. Also, cover part 117 comes into contact with the upper surface of the liquid in the passage part 116 above the liquid containers 110. More specifically, the liquid is sandwiched from above and below by liquid containers 110 and cover part 117. Thus, liquid containers 110 and passage part 116 may be disposed so as to be exposed to the upper surface of sample analysis cartridge main body 100a and covered with cover part 117. Accordingly, permanent magnet 520 can come close to liquid containers 110 and passage part 116 from outside sample analysis cartridge 100. Thus, stronger magnetic force can be generated to act on magnetic particles 191 for efficient transportation of magnetic particles 191.

Cover part 117 includes a flat sheet member, for example. Cover part 117 may be formed using a material having a hydrophobic surface on the liquid container 110 side. Thus, effective action of surface tension of the liquid can be achieved. The hydrophobic material may be a coating material provided on the surface of the sheet member of cover part 117. The sheet member itself included in cover part 117 may be formed using a hydrophobic material.

(Liquid Reaction Part)

Figure 10A:
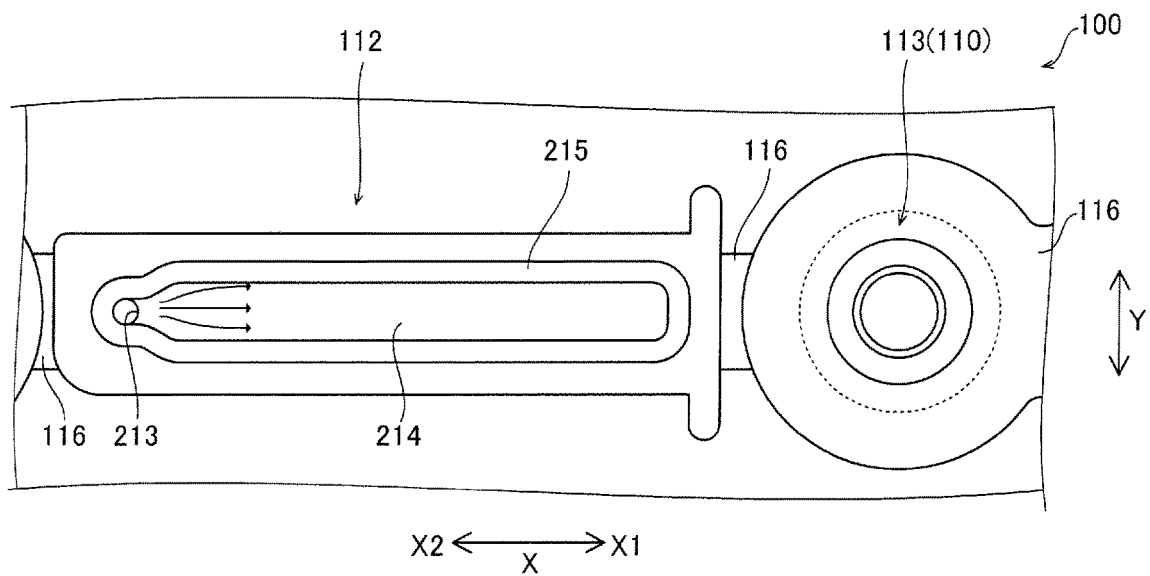
FIG. 10A is a plan view and FIG. 10B is a cross-sectional view illustrating a configuration example of a liquid reaction part.
Figure 10B:
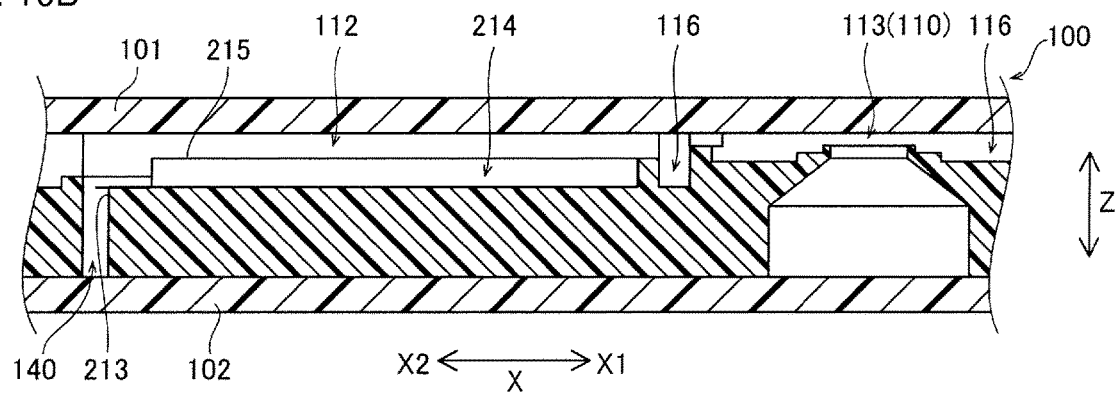

FIG. 10 illustrates a configuration example of liquid reaction part 112. In sample analysis cartridge 100, the sample flowing in from blood cell separator 120 is mixed with the R1 reagent on sample flow path 140, and the mixed liquid is discharged to liquid reaction part 112.

Liquid reaction part 112 has inlet 213 for supplying the mixed liquid of the sample and the R1 reagent to the inside. Inlet 213 is connected to sample flow path 140 and is disposed in a peripheral portion of liquid disposition part 214. FIG. 10 illustrates a configuration example where liquid disposition part 214 extends linearly in the X direction. In this case, inlet 213 is disposed at the end of liquid disposition part 214. Step part 215 is provided along the peripheral edge of liquid disposition part 214 including inlet 213. Inlet 213 is an opening formed in the surface of liquid disposition part 214, for example.

Figure 11:
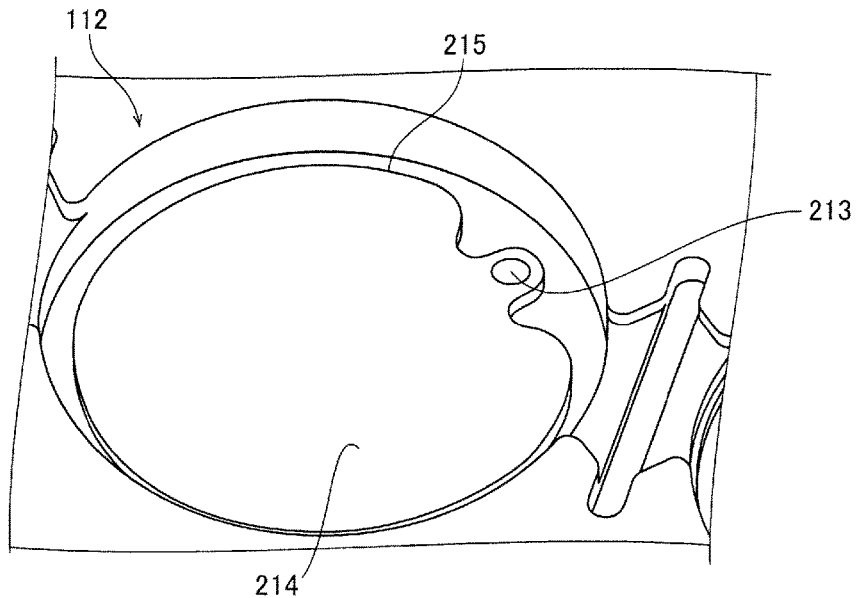
FIG. 11 is a diagram illustrating another configuration example of the liquid reaction part.

FIG. 11 illustrates another configuration example of liquid reaction part 112.

As illustrated in FIG. 11, liquid reaction part 112 may have a shape other than the linearly extending shape. Here, liquid reaction part 112 has approximately circular liquid disposition part 214. Inlet 213 is disposed in the surface of a peripheral portion of liquid disposition part 214. Step part 215 is formed in a peripheral portion of liquid disposition part 214.

(Third Liquid Container)

Figure 12A:
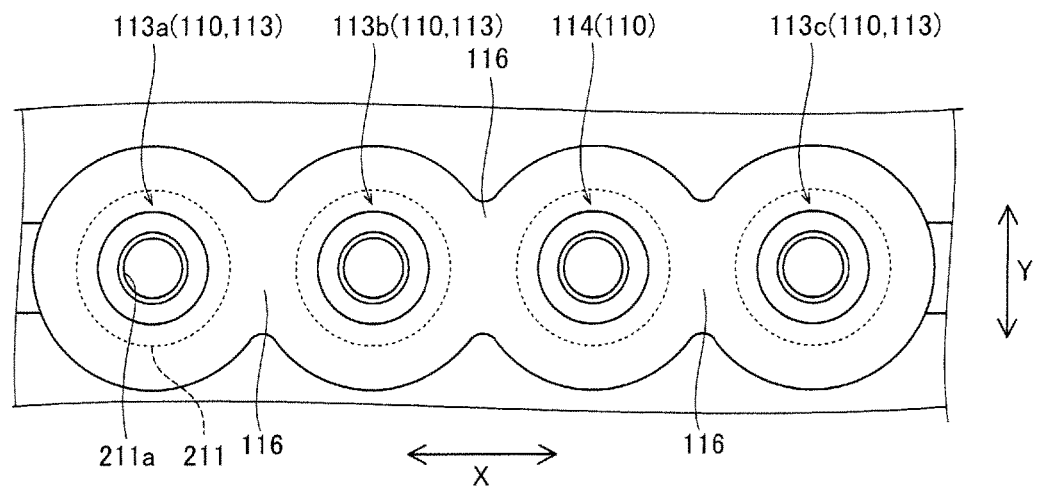
FIG. 12A is a plan view and FIG. 12B is a cross-sectional view illustrating a configuration example of a third liquid container.

As illustrated in FIG. 12A, third liquid container 113 is disposed on the upstream side or downstream side of the liquid container in which magnetic particles 191 transported by the magnetic force reacts with the reagent. Third liquid containers 113 may be disposed on both of the upstream side and downstream side of the liquid container. Note that the upstream side and downstream side described here mean a transportation direction of magnetic particles 191 and not the direction in which the liquid flows. Third liquid containers 113 may be arranged on the upstream side or downstream side of the liquid container. For example, third liquid container 113a and third liquid container 113b are on the upstream side of second liquid container 114, and third liquid container 113c is on the downstream side of second liquid container 114.

Figure 12B:
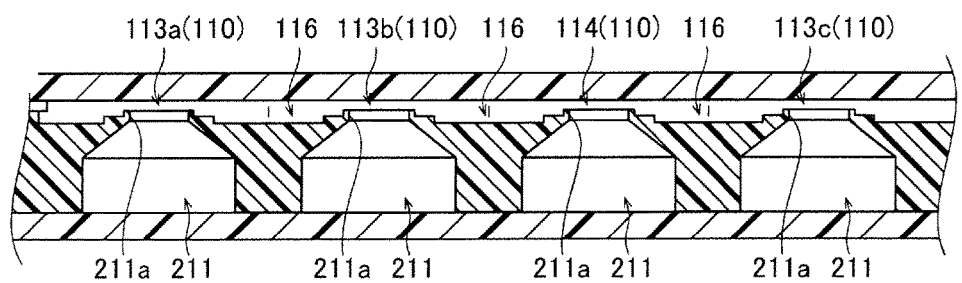

As illustrated in FIG. 12B, each of third liquid containers 113a to 113c includes liquid storage part 211 having opening 211a. Magnetic particles 191 can be dispersed into a larger amount of cleaning liquid by transporting magnetic particles 191 into liquid storage parts 211 through openings 211a. Thus, cleaning efficiency can be improved.

(Second Liquid Container and Fourth Liquid Container)

For second liquid container 114, the same configuration as that of third liquid container 113 can be adopted. By providing liquid storage part 211 in second liquid container 114, the amount of the R3 reagent in which magnetic particles 191 are to be dispersed can be increased. Thus, reaction efficiency can be improved. The same applies to fourth liquid container 115.

(Transportation of Magnetic Particles)

In this embodiment, sample analyzer 500 transports magnetic particles 191 through the gas-phase space in passage part 116 between liquid containers 110. During the process of transporting magnetic particles 191 between liquid containers 110, the antibody, antigen and the like contained in the liquid adhere to magnetic particles 191, and reaction required for the assay progresses. Thus, it is possible to suppress the mixing of the liquid contained in liquid container 110 into the liquid contained in another liquid container 110 by the movement of magnetic particles 191.

Figure 13:
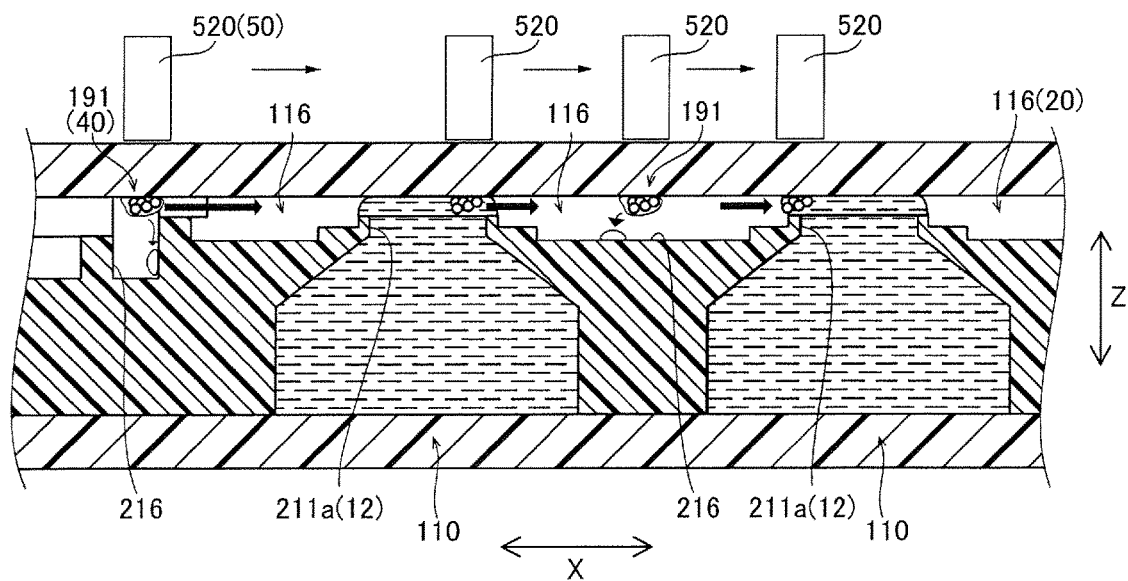
FIG. 13 is a cross-sectional view for explaining transportation of magnetic particles.

FIG. 13 illustrates details of the transportation of magnetic particles 191 between liquid containers 110.

Sample analyzer 500 moves permanent magnet 520 close to liquid container 110 in sample analysis cartridge 100, thereby aggregating magnetic particles 191 in the liquid on the surface of liquid container 110. Sample analyzer 500 moves permanent magnet 520 to transport magnetic particles 191 aggregated on the gas-liquid interface. Sample analyzer 500 moves permanent magnet 520 to transport the aggregated magnetic particles 191 to the passage part 116 from inside the liquid. The magnetic force of permanent magnet 520 transports the aggregated magnetic particles 191 to passage part 116 from inside the liquid beyond the gas-liquid interface. Sample analyzer 500 further moves permanent magnet 520 to transport aggregated magnetic particles 191 to another liquid container 110.

Liquid containers 110 associated with the transportation of magnetic particles 191 may be arranged linearly in the longitudinal direction of sample analysis cartridge 100. In the configuration example illustrated in FIG. 4, first liquid container 111, liquid reaction part 112, third liquid container 113, second liquid container 114, and fourth liquid container 115 are linearly arranged. By linearly arranging liquid containers 110, it is possible to suppress magnetic particles 191 remaining in liquid containers 110 and passage part 116.

The liquid may adhere to magnetic particles 191 transported to passage part 116 from inside the liquid. As illustrated in FIG. 13, a structure to remove the liquid adhering to magnetic particles 191 may be provided in passage part 116 between liquid containers 110. For example, as such a structure, grooves 216 may be provided by denting the surface of passage part 116. Thus, a structure is realized, in which the liquid adhering to magnetic particles 191 is likely to fall onto the bottom of groove 216 from passage part 116. Note that, as described above, when grooves 216 are provided, it is possible to further suppress the mixing of the liquid leaking from liquid container 110 into the liquid contained in another liquid container 110 by the movement of magnetic particles 191.

(Transportation of Magnetic Particles to Respective Liquid Containers)

Figure 14:
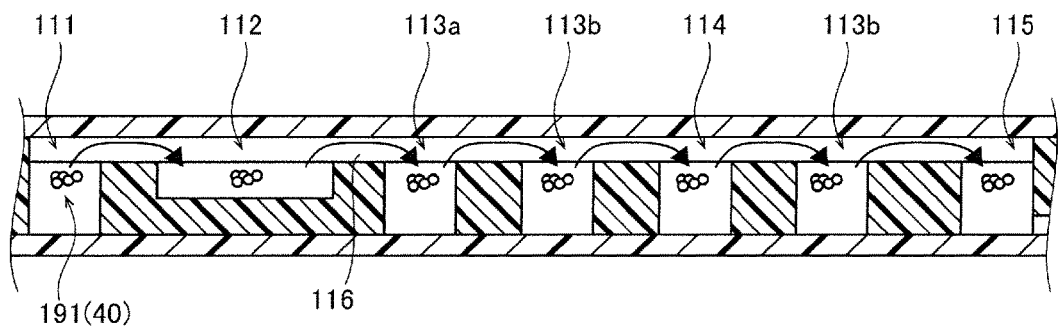
FIG. 14 is a cross-sectional view for explaining transportation of the magnetic particles between the liquid containers.

Here, description is given of transportation of magnetic particles 191 between adjacent liquid containers. In a configuration example illustrated in FIG. 14, magnetic particles 191 are transported by the magnetic force to liquid reaction part 112, third liquid container 113a, third liquid container 113b, second liquid container 114, third liquid container 113c, and fourth liquid container 115 in this order, starting from first liquid container 111 on the upstream side in the transportation direction.

Liquid reaction part 112 and third liquid container 113a are adjacent to each other through passage part 116. Magnetic particles 191 are transported from liquid reaction part 112 to third liquid container 113a through passage part 116. Unwanted substances adhering to magnetic particles 191 are dispersed into the cleaning liquid. Thus, only a coupled body of test substance 190 and magnetic particle 191 can be taken out of liquid reaction part 112 and transported into the cleaning liquid in third liquid container 113a. Thus, the unwanted substances mixed into the cleaning liquid together with the magnetic particles can be reduced. Therefore, the cleaning treatment can be efficiently performed. The unwanted substances are substances not required for measurement of test substance 190, such as components other than test substance 190 contained in the sample and components unreacted with test substance 190 contained in the reagent.

Third liquid container 113a and third liquid container 113b are adjacent to each other through passage part 116. Magnetic particles 191 are transported to third liquid container 113b from third liquid container 113a. More specifically, magnetic particles 191 after cleaning treatment are subjected again to cleaning treatment in another third liquid container 113b through passage part 116. Thus, the cleaning treatment can be more effectively performed.

Third liquid container 113b and second liquid container 114 are adjacent to each other through passage part 116. Magnetic particles 191 are transported to second liquid container 114 from third liquid container 113b. Thus, it is possible to suppress transporting of some of the unwanted substances dispersed into the cleaning liquid in third liquid container 113b to second liquid container 114 together with magnetic particles 191. In second liquid container 114, magnetic particles 191 carry complex 190c of test substance 190 and labeled substance 193.

Note that second liquid container 114 is adjacent to third liquid containers 113. Magnetic particles 191 are transported to third liquid container 113b on the upstream side, second liquid container 114, and third liquid container 113c on the downstream side. Thus, mixing of unwanted substances into second liquid container 114 and carryover of unwanted substances from second liquid container 114, such as unreacted labeled substance 193 that has formed no complex 190c with test substance 190 can be efficiently suppressed.

Third liquid container 113c and fourth liquid container 115 are adjacent to each other. Magnetic particles 191 carrying complex 190c are transported to fourth liquid container 115 through passage part 116, and thus dispersed into the buffer liquid. Accordingly, the amount of unwanted substances adhering to magnetic particles 191 carrying complex 190c can be reduced. Thus, it is possible to suppress the transporting of the unwanted substances such as unreacted labeled substance 193 to fourth liquid container 115 together with magnetic particles 191.

(Agitation Operation)

An agitation operation using permanent magnet 520 is described. In the agitation operation, magnetic particles 191 are dispersed in the liquid by periodically changing the direction or strength of magnetic force acting on magnetic particles 191, for example. FIG. 15 illustrates an agitation operation for reacting magnetic particles 191 with an antigen-antibody reactant in liquid reaction part 112.

Figure 15A:
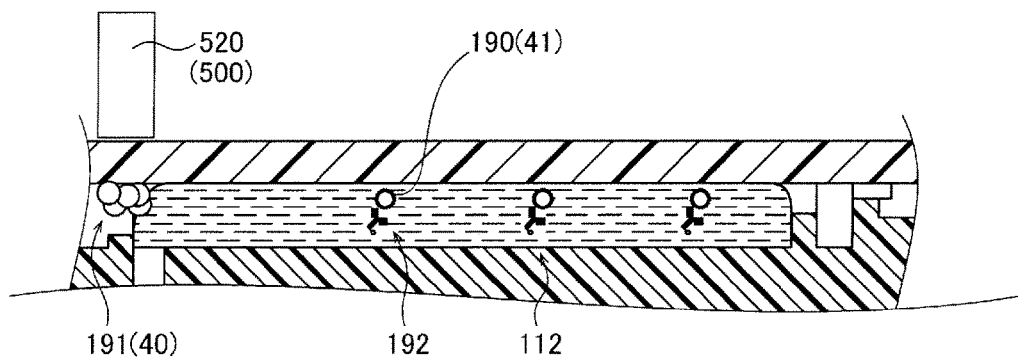
FIG. 15A is a cross-sectional view during magnetic collection.

In FIG. 15A, sample analyzer 500 uses permanent magnet 520 to transport magnetic particles 191 from first liquid container 111 to liquid reaction part 112. Sample analyzer 500 moves permanent magnet 520 close to sample analysis cartridge 100 to transport magnetic particles 191 in an aggregated state.

Figure 15B:
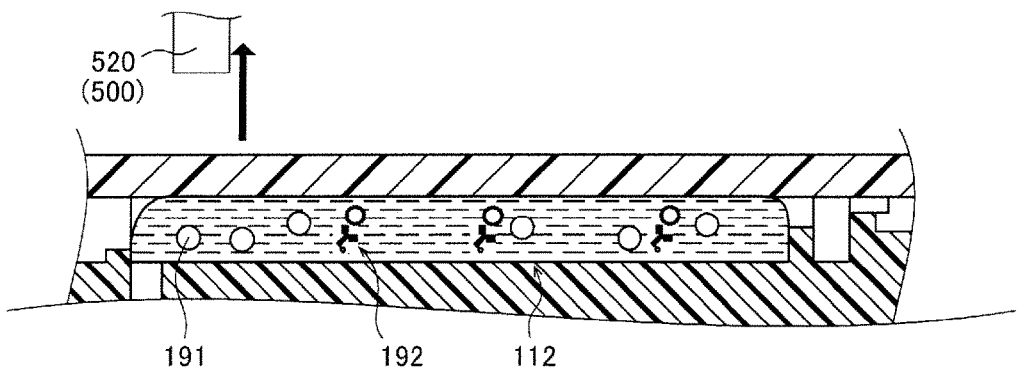
FIG. 15B is a cross-sectional view during dispersion.

In FIG. 15B, sample analyzer 500 separates permanent magnet 520 from sample analysis cartridge 100 to disperse magnetic particles 191 in liquid reaction part 112. More specifically, the strength of the magnetic force acting on magnetic particles 191 is changed. The agitation of magnetic particles 191 is facilitated by dispersing magnetic particles 191 in liquid reaction part 112.

Figure 15C:
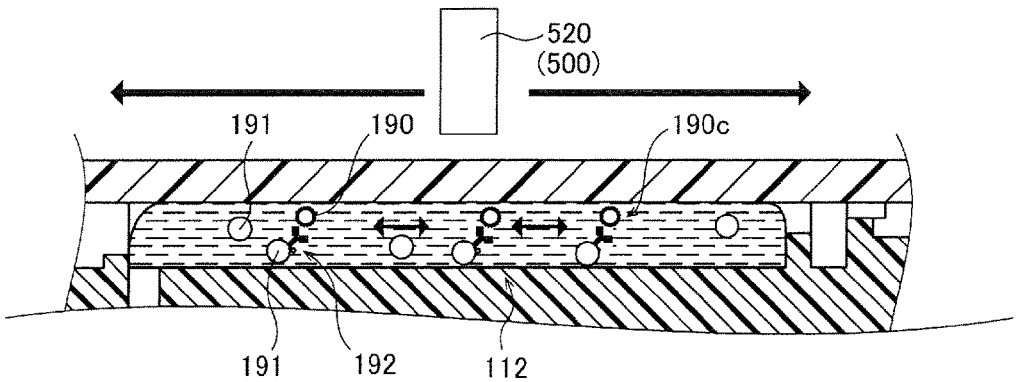
FIG. 15C is a cross-sectional view during agitation for explaining an agitation operation in the liquid reaction part.

In FIG. 15C, sample analyzer 500 moves permanent magnet 520 separated from sample analysis cartridge 100 to agitate dispersed magnetic particles 191. Sample analyzer 500 agitates magnetic particles 191 by moving the magnet in the width direction or length direction of sample analysis cartridge 100 or in a circular orbit.

By periodically repeating such operations, magnetic particles 191 are dispersed in the liquid. Thus, the reaction can be efficiently progressed. In this embodiment, a magnet with strong magnetic force, such as a permanent magnet, is preferably used to transport magnetic particles 191 beyond the surface tension of the liquid. Therefore, when sample analysis cartridge 100 is close to permanent magnet 520, magnetic particles 191 are aggregated, inhibiting efficient agitation. The agitation of magnetic particles 191 can be facilitated by controlling the distance between sample analysis cartridge 100 and permanent magnet 520.

FIG. 16 illustrates another agitation example according to this embodiment.

Figure 16A:
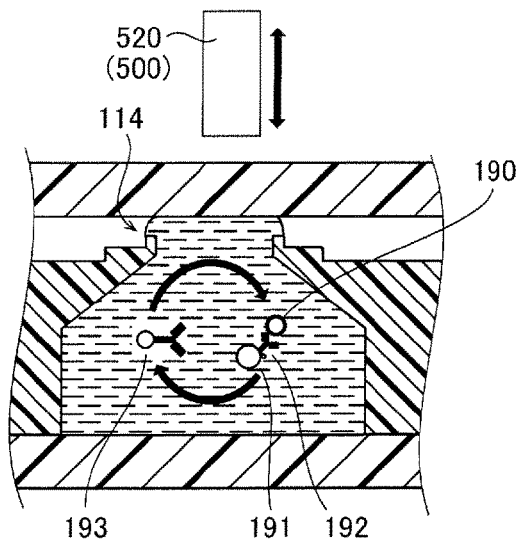
FIG. 16A is a diagram illustrating an agitation operation example and FIG. 16B is a diagram illustrating another agitation operation example in a second liquid container.

FIG. 16A illustrates an agitation operation example in second liquid container 114. In this agitation operation example, magnetic particles 191 are moved up and down in liquid container 110. Sample analyzer 500 moves permanent magnet 520 in the thickness direction of sample analysis cartridge 100 in second liquid container 114. As a result, the strength of the magnetic force acting on magnetic particles 191 is changed. By moving permanent magnet 520 in the thickness direction of sample analysis cartridge 100, a coupled body of labeled substance 193 and magnetic particle 191 is agitated in a depth direction of second liquid container 114. The agitation is facilitated entirely in the depth direction of second liquid container 114 rather than agitating only in the surface of second liquid container 114.

Figure 16B:
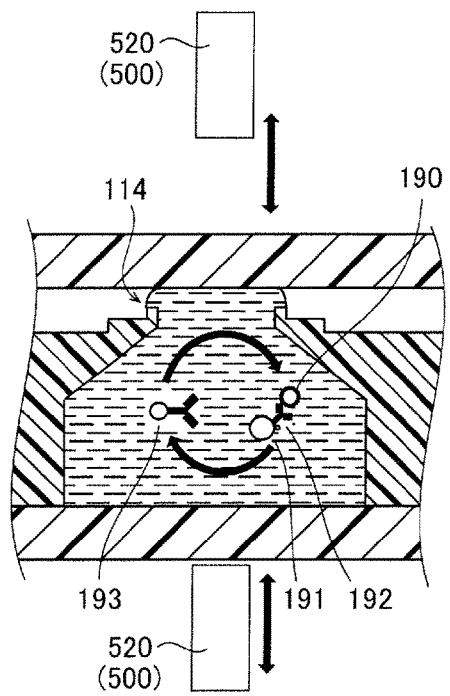

FIG. 16B illustrates another agitation operation example in second liquid container 114. In the example of FIG. 16B, permanent magnets 520 are disposed on the upper surface side and lower surface side of sample analysis cartridge 100, respectively. By alternately moving permanent magnets 520 close to above and below liquid container 110, magnetic particles 191 are moved in a vertical direction within liquid container 110. In this case, the direction in which magnetic particles 191 are attracted by the strong magnetic force is alternately reversed in the thickness direction of sample analysis cartridge 100. The permanent magnets 520 on the both surfaces of sample analysis cartridge 100 are moved to further facilitate the agitation of the coupled body of labeled substance 193 and magnetic particle 191.

(Configuration of Air Chamber)

Figure 17:
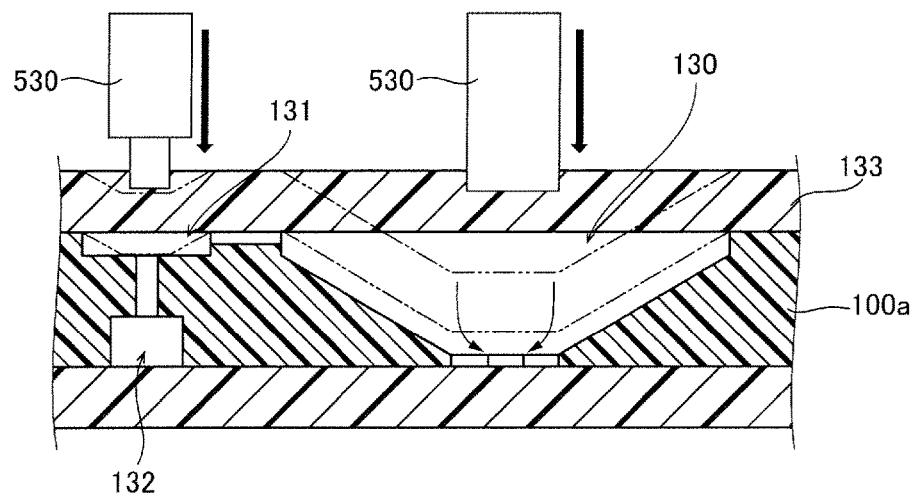
FIG. 17 is a cross-sectional view illustrating a configuration example of an air chamber and a valve part.

FIG. 17 illustrates a configuration example of air chamber 130.

Air chamber 130 is connected to valve part 131 and a portion of an air supply destination. Valve part 131 is connected to air chamber 130 and air flow path 132 connected to the outside of sample analysis cartridge 100, respectively. The air outside the cartridge is taken into air chamber 130 from air flow path 132 through valve part 131.

Air chamber 130 and valve part 131 have a structure for activation by plunger 530. For example, air chamber 130 and valve part 131 are each formed into a recessed shape in the surface of cartridge main body 100a so as to have an opening in the upper part thereof, and covered with sheet 133 that is an elastic member.

Valve part 131 can close the connection portion with air flow path 132 by plunger 530 entering the inside from the outside through sheet 133. Air chamber 130 is filled with air. Air chamber 130 can discharge the internal air to the supply destination flow path by plunger 530 pushing sheet 133 into air chamber 130 from the outside. Sample analyzer 500 discharges the air in air chamber 130 to the supply destination flow path by using plunger 530 to close valve part 131 and push sheet 133 into air chamber 130. Here, the operation of pushing sheet 133 into air chamber 130 by using plunger 530 is described as "activating air chamber 130". The operation of pushing sheet 133 into valve part 131 by using plunger 530 is described as "closing valve part 131".

In a state where valve part 131 is not closed, air chamber 130 comes into contact with the air outside the cartridge through valve part 131 and air flow path 132. When sample analysis cartridge 100 is heated by heat blocks 510, the air in air chamber 130 expands. When the air in air chamber 130 expands, an increase in internal pressure of air chamber 130 causes the air to flow out to the flow path of air supply destination. As a result, the liquid in sample analysis cartridge 100 may be unintentionally operated. A change in internal pressure due to the expansion of the air in air chamber 130 is suppressed by air chamber 130 coming into contact with the air outside sample analysis cartridge 100 through air flow path 132. Thus, unintentional operation of the liquid in sample analysis cartridge 100 can be suppressed.

Air chambers 130 and valve parts 131 may be provided according to the number of the air supply destinations. Sample analyzer 500 may include the same number of plungers 530 as those of air chambers 130 and valve parts 131 or may include a smaller number of plunger 530 than those of air chambers 130 and valve parts 131. In such a case, air chambers 130 and valve parts 131 to be activated may be switched by moving plungers 530. The sample analyzer can be reduced in size for the reduction in the number of plungers 530.

The arrangement positions of air chambers 130 and valve parts 131 may be set according to the configuration of sample analysis cartridge 100. When plunger 530 is moved, air chambers 130 or valve parts 131 may be linearly arranged. Accordingly, plunger 530 needs only be linearly moved in the arrangement direction. Thus, the movement mechanism can be simplified to reduce the size of the sample analyzer.

(Flow Path Structure)

Sample analysis cartridge 100 has a flow path structure that facilitates mixing of liquids on a flow path.

<Sample Flow Path>

Figure 18:
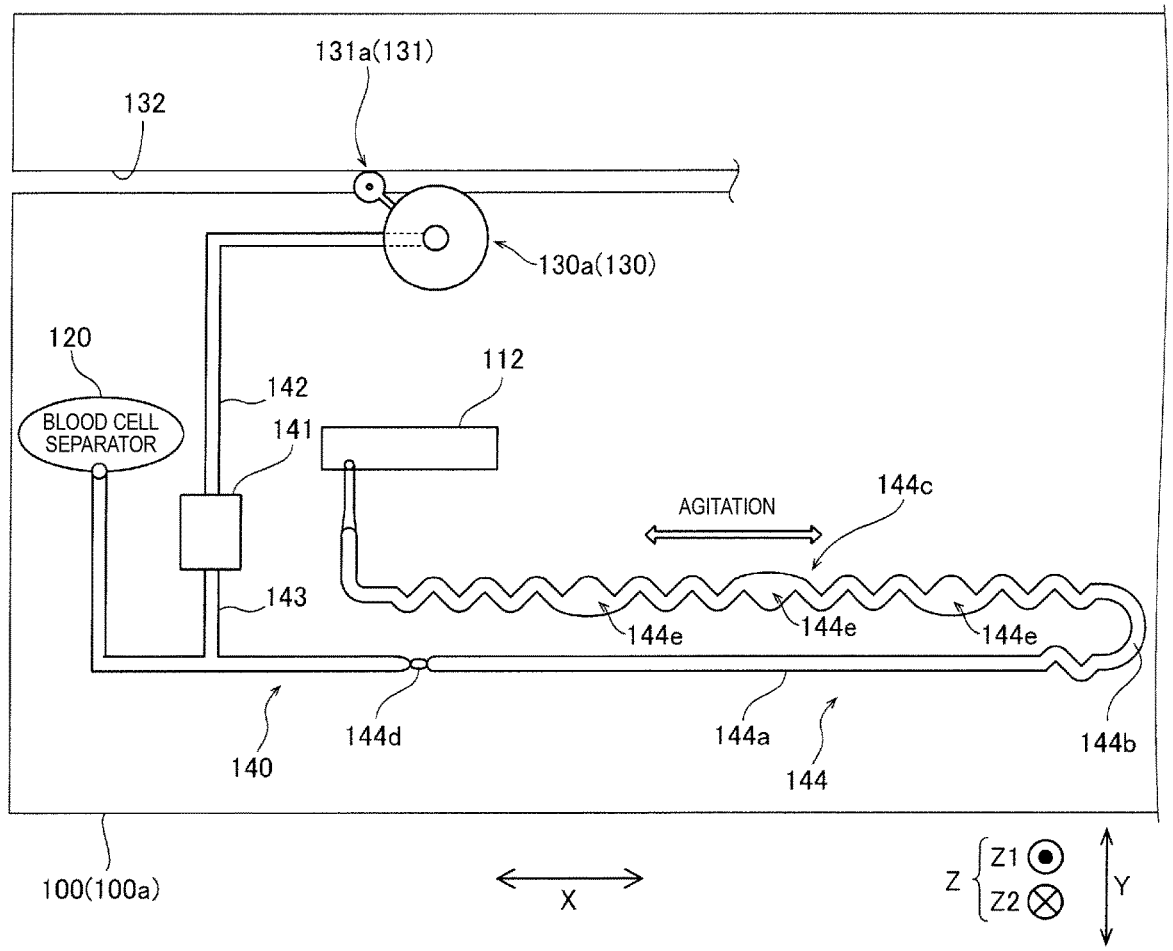
FIG. 18 is a schematic plan view illustrating a configuration example of a sample flow path.

Next, a configuration of sample flow path 140 is described. Sample analysis cartridge 100 includes sample flow path 140 for transporting a mixed liquid of a reagent and a sample containing test substance 190 to liquid reaction part 112. FIG. 18 is a schematic diagram of the sample flow path. On sample flow path 140, air chamber 130a agitates the mixed liquid of the sample and the reagent by the air pressure in sample flow path 140, and transports the mixed liquid to liquid reaction part 112. Thus, since the mixed liquid of the sample and the reagent can be agitated in the sample flow path 140, the mixed liquid can be supplied to liquid reaction part 112 in a state where test substance 190 and the reagent are sufficient reacted.

Sample flow path 140 includes, for example, R1 reagent tank 141, first portion 142, second portion 143, and mixing part 144. R1 reagent tank 141 has one end connected to air chamber 130a through first portion 142. R1 reagent tank 141 has the other end connected to blood cell separator 120 through second portion 143. R1 reagent tank 141 is connected to liquid reaction part 112 through mixing part 144. R1 reagent tank 141 stores the R1 reagent. In this embodiment, sample analyzer 500 uses air chamber 130a to alternately generate a positive pressure and a negative pressure, thereby moving back and forth a mixed liquid of the sample and the R1 reagent within sample flow path 140. Thus, the mixed liquid can be efficiently agitated within sample flow path 140. The volume of sample flow path 140 is larger than that of the mixed liquid. Therefore, the mixed liquid can be easily moved back and forth within sample flow path 140.

Mixing part 144 has one end connected to a joint portion between second portion 143 and a flow path from blood cell separator 120. Mixing part 144 has the other end connected to liquid reaction part 112. Mixing part 144 includes straight part 144a, bent part 144b, and meander part 144c.

Straight part 144a partially overlaps with meander part 144c as seen from the short direction of sample analysis cartridge 100. Straight part 144a has narrow flow path part 144d, for example. Narrow flow path part 144d can stop the sample flowing through sample flow path 140 at narrow flow path part 144d. Mixing part 144 does not have to include straight part 144a.

Bent part 144b connects straight part 144a to meander part 144c. Bent part 144b is formed into an approximately U-shape. In a schematic view, sample flow path 140 is bent approximately 180 degrees at bent part 144b. Thus, the movement distance of the mixed liquid can be increased, and thus the mixed liquid can be efficiently mixed. Mixing part 144 does not have to include bent part 144b.

In a planar view, a sine-wave shape or the like can be adopted as the shape of meander part 144c. The agitation of the mixed liquid can be facilitated by meander part 144c changing the circulation direction of the mixed liquid.

Meander part 144*c* includes dilated parts 144*e*. Dilated parts 144*e* are formed by increasing the cross-sectional area of meander part 144*c* on the plane having a normal line in the flow path direction of the mixed liquid. Dilated parts 144*e* accumulate the flow of the mixed liquid and capture air bubbles generated in the mixed liquid flowing through the flow path. Dilated parts 144*e* can remove the air bubbles from the mixed liquid flowing through meander part 144*c*. Moreover, dilated parts 144*e* can complicate the flow of the mixed liquid with changes in cross-sectional area, thereby facilitating the agitation of the mixed liquid. Mixing part 144 does not have to include meander part 144*c*. Meander part 144*c* may include only one dilated part 144*e*. Alternatively, meander part 144*c* does not have to include dilated parts 144*e*.

Mixing part 144 is connected to liquid reaction part 112 from the back surface side of sample analysis cartridge 100, for example. Thus, the mixed liquid of the sample and the R1 reagent can be discharged to liquid reaction part 112 from below.

<Mixed Liquid Flow Path>

Figure 19:
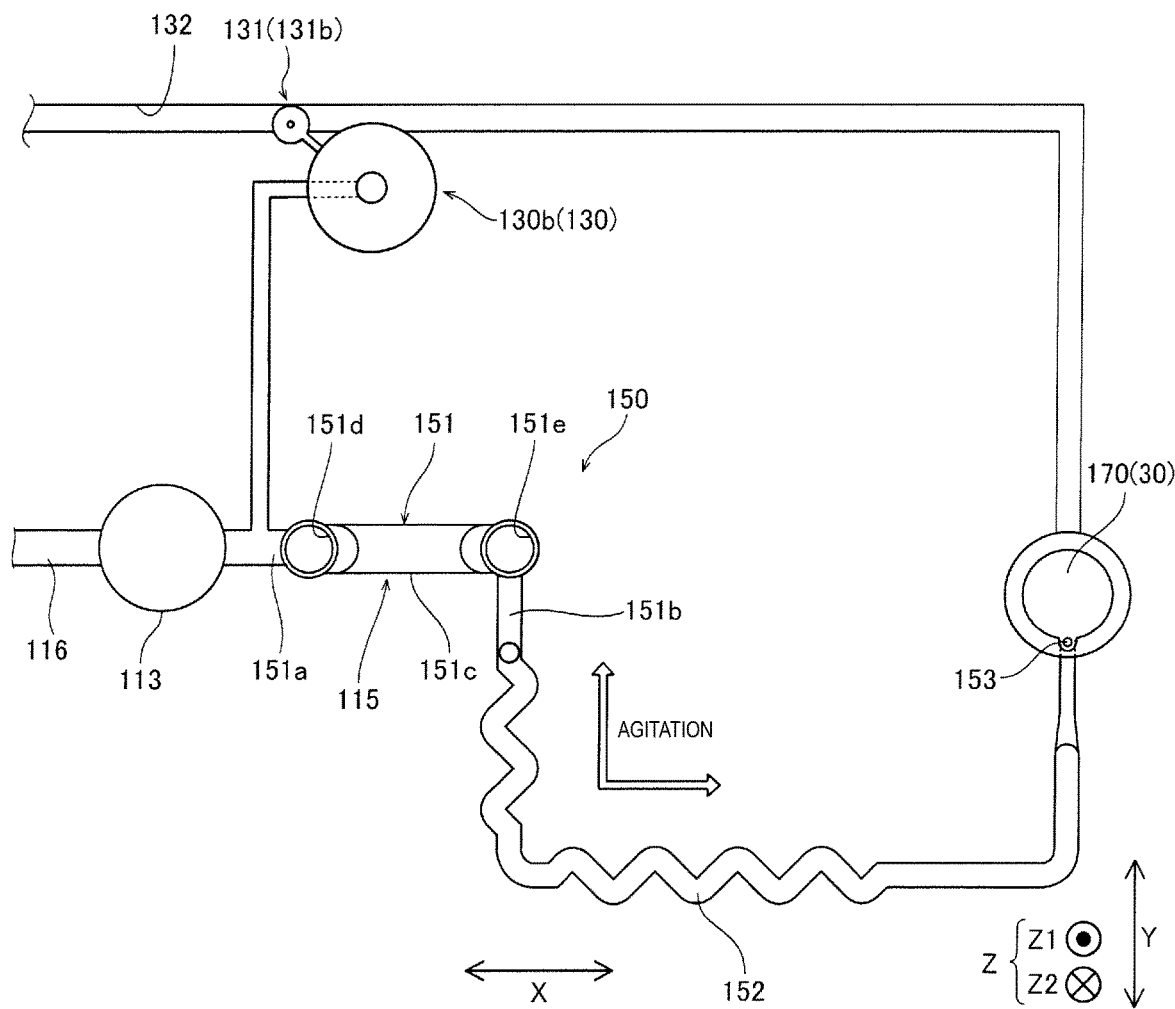
FIG. 19 is a schematic plan view illustrating a configuration example of a mixed liquid flow path.

FIG. 19 is a schematic diagram of mixed liquid flow path 150. Mixed liquid flow path 150 is formed in a region between passage part 116 and detection tank 170, and connects passage part 116 to detection tank 170. Mixed liquid flow path 150 includes, for example, dispersion portion 151, first portion 152, and second portion 153. Mixed liquid flow path 150 has a structure to disperse complex 190*c* containing magnetic particles 191 and labeled substance 192 into the buffer liquid that is the R4 reagent. On mixed liquid flow path 150, air chamber 130*b* transports the mixed liquid of the buffer liquid and magnetic particles 191 carrying complex 190*c* to detection tank 170. Thus, magnetic particles 191 transported in an aggregated state by magnetic force are dispersed in the buffer liquid and transported to detection tank 170 while being dispersed in the buffer liquid. Accordingly, test substance 190 can be easily detected in detection tank 170.

Mixed liquid flow path 150 joins passage part 116. Mixed liquid flow path 150 agitates the mixed liquid of complex 190*c* and the R4 reagent by moving the mixed liquid back and forth in mixed liquid flow path 150 with the air pressure. In this embodiment, the mixed liquid is moved back and forth within mixed liquid flow path 150 by air chamber 130*b* alternately generating a positive pressure and a negative pressure. Thus, the mixed liquid can be efficiently agitated in the flow path. The volume of mixed liquid flow path 150 is larger than the volume of the mixed liquid. Thus, the mixed liquid can be easily moved back and forth in the mixed liquid flow path 150.

Figure 20:
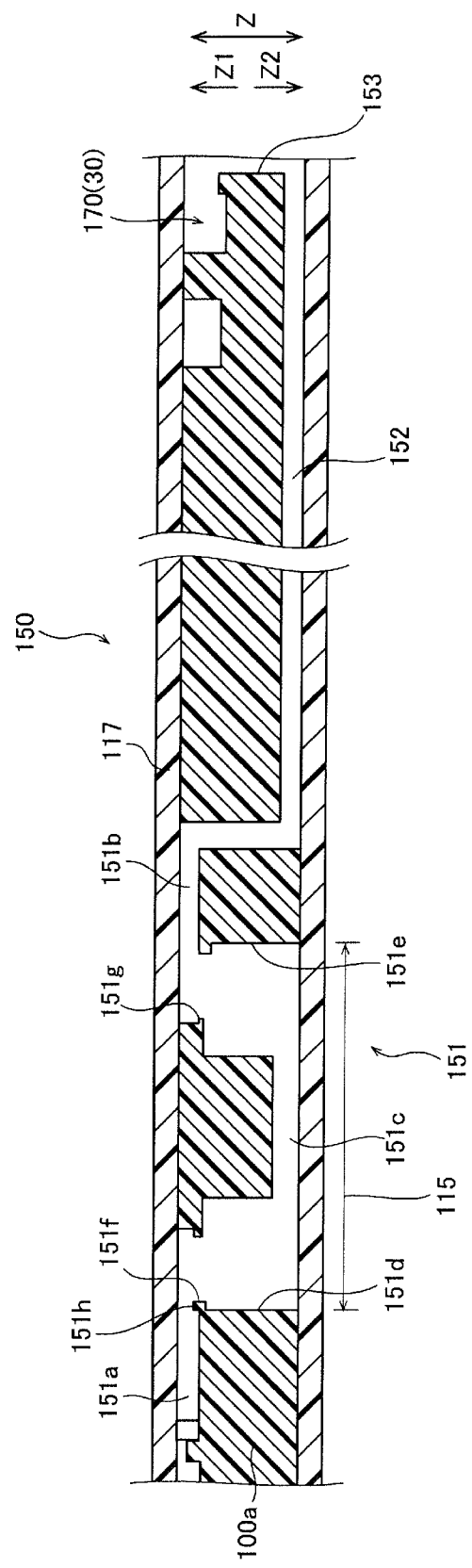
FIG. 20 is a schematic cross-sectional view along the mixed liquid flow path illustrated in FIG. 19.

FIG. 20 is a schematic cross-sectional view along mixed liquid flow path 150. Dispersion portion 151 includes connection portion 151*a* connected to passage part 116 and first portion connection portion 151*b* connected to first portion 152. Dispersion portion 151 includes fourth liquid container 115.

Fourth liquid container contains the R4 reagent. Fourth liquid container 115 is connected to connection portion 151*a* at one side portion 151*d* extending in the thickness direction (Z direction) of cartridge main body 100*a*. Fourth liquid container 115 is connected to first portion connection portion 151*b* at the other side portion 151*e* extending in the Z direction. At an upper end of one side portion 151*d*, reduced diameter part 151*f* is formed. At an upper end of the other side portion 151*e*, reduced diameter part 151*g* is formed.

Step 151*h* protruding in a Z1 direction is formed on reduced diameter part 151*f*.

First portion 152 is disposed at a position lower than detection tank 170 in the Z direction (thickness direction of sample analysis cartridge 100). First portion 152 has one end connected to dispersion portion 151 and the other end connected to second portion 153. First portion 152 is formed so as to extend along the surface of cartridge main body 100*a*. Thus, the mixed liquid of complex 190*c* and the R4 reagent can be moved within a wide range and efficiently agitated.

Second portion 153 is disposed at a position lower than detection tank 170 in the Z direction (thickness direction of sample analysis cartridge 100). Second portion 153 extends in the Z direction. Second portion 153 has one end connected to first portion 152 and the other end connected to detection tank 170. Thus, the mixed liquid of complex 190*c* and the R4 reagent can be discharged to detection tank 170 from below.

Referring back to FIG. 19, first portion 152 of mixed liquid flow path 150 may be formed into a meandering shape in a planar view, for example. Thus, mixed liquid flow path 150 can be easily elongated. As a result, the mixed liquid of complex 190*c* and the R4 reagent can be efficiently agitated within mixed liquid flow path 150. As the meandering shape of first portion 152 in mixed liquid flow path 150, a sine-wave shape or the like can be adopted. Thus, mixed liquid flow path 150 can be easily formed into the meandering shape, and the mixed liquid of complex 190*c* and the R4 reagent can be efficiently agitated within mixed liquid flow path 150.

<Other Configuration Examples of Mixed Liquid Flow Path>

Figure 21:
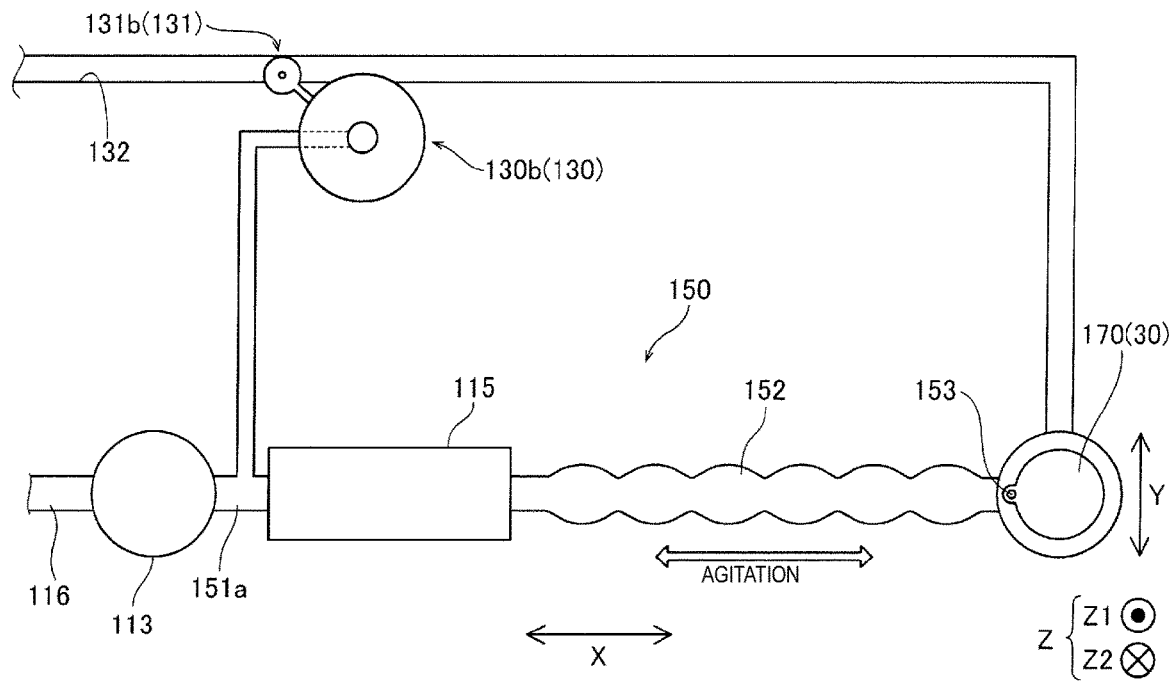
FIG. 21 is a first diagram illustrating another configuration example regarding the mixed liquid flow path.

FIGS. 21 to 25 illustrate other configuration examples of mixed liquid flow path 150. As illustrated in FIG. 21, first portion 152 of mixed liquid flow path 150 may be formed such that the cross-section perpendicular to the extending direction of mixed liquid flow path 150 differs in the extending direction of mixed liquid flow path 150. Thus, unlike the case where mixed liquid flow path 150 is formed into the meandering shape, mixed liquid flow path 150 can be formed in a compact size, and the mixed liquid of complex 190*c* and the R4 reagent can be efficiently agitated within mixed liquid flow path 150.

Figure 22:
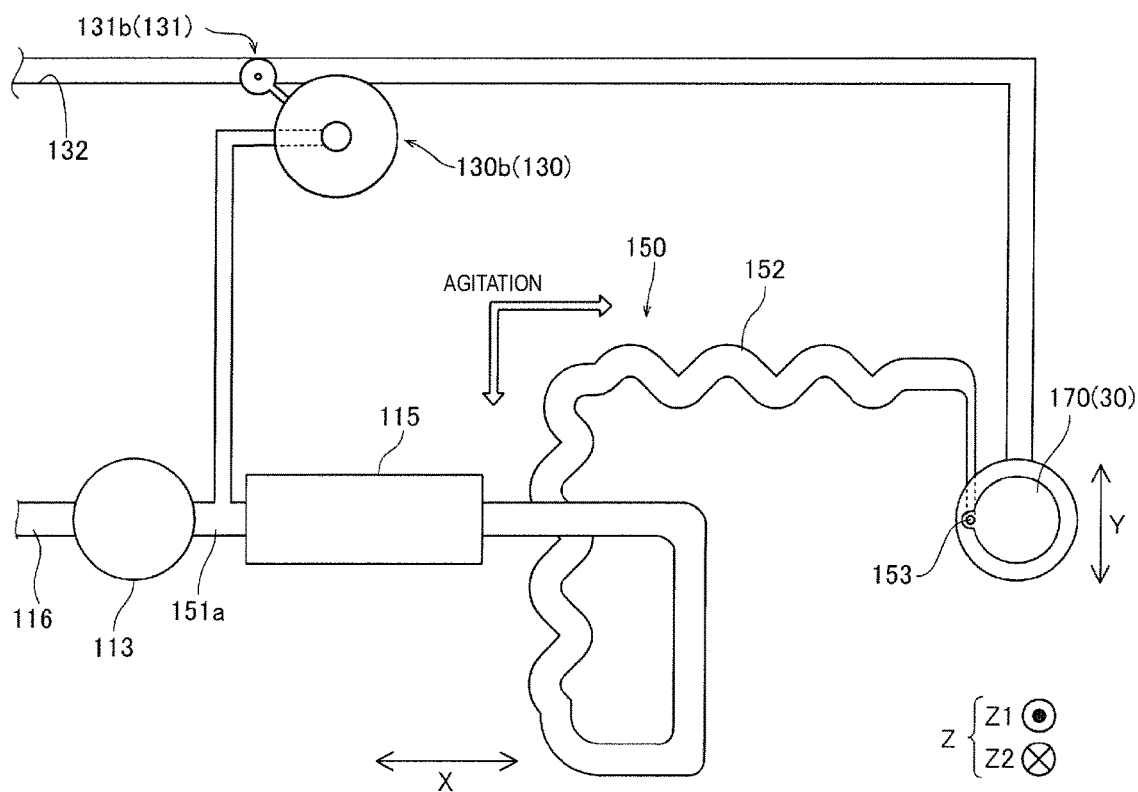
FIG. 22 is a second diagram illustrating another configuration example regarding the mixed liquid flow path.

As illustrated in FIG. 22, mixed liquid flow path 150 may have a partially overlapping part by forming mixed liquid flow path 150 into a three-dimensionally intersecting shape.

Figure 23:
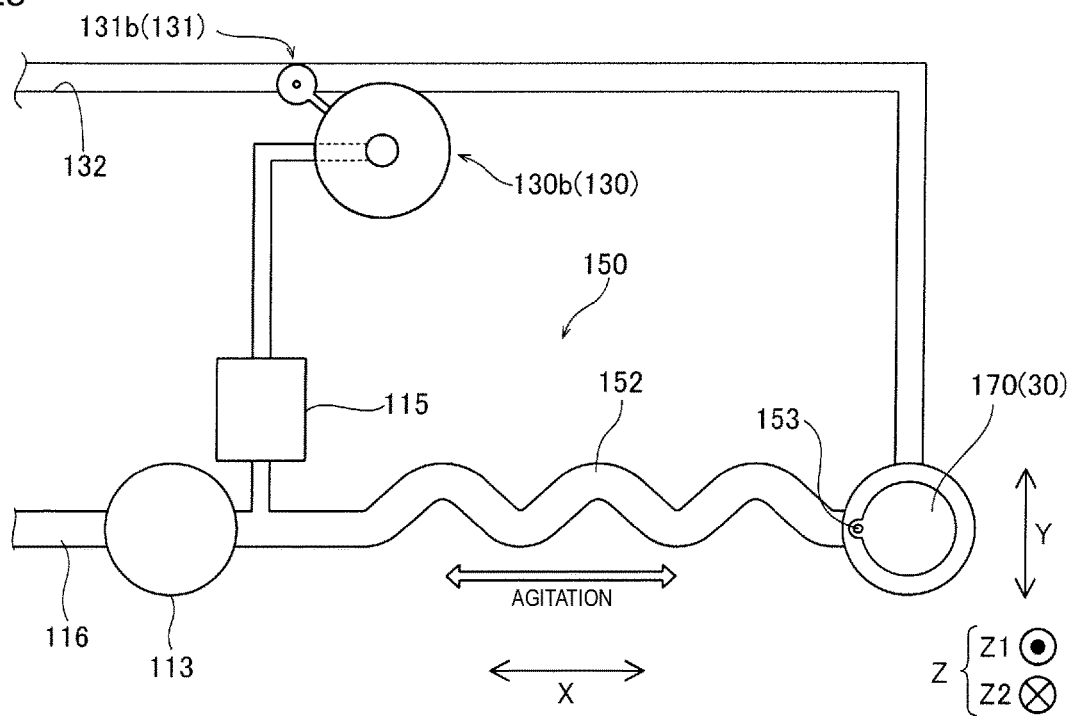
FIG. 23 is a third diagram illustrating another configuration example regarding the mixed liquid flow path.

As illustrated in FIG. 23, fourth liquid container 115 may be disposed in a flow path portion connecting air chamber 130 to mixed liquid flow path 150.

Figure 24:
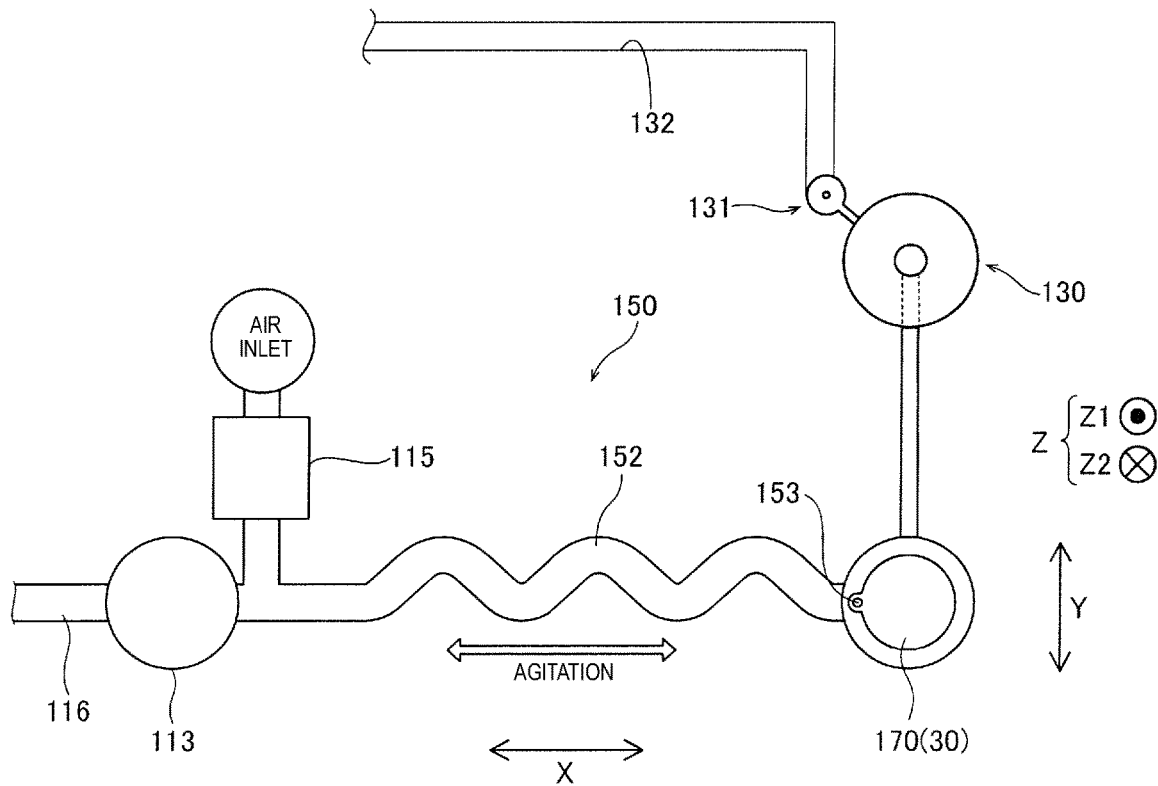
FIG. 24 is a fourth diagram illustrating another configuration example regarding the mixed liquid flow path.

As illustrated in FIG. 24, fourth liquid container 115 may be configured to supply the R4 reagent to detection tank 170 by using a negative pressure from air chamber 130. In this case, fourth liquid container 115 has one side (upstream side) connected to an air inlet. Air chamber 130 is connected to detection tank 170, and the negative pressure generated in air chamber 130 discharges the R4 reagent to first portion 152.

Figure 25:
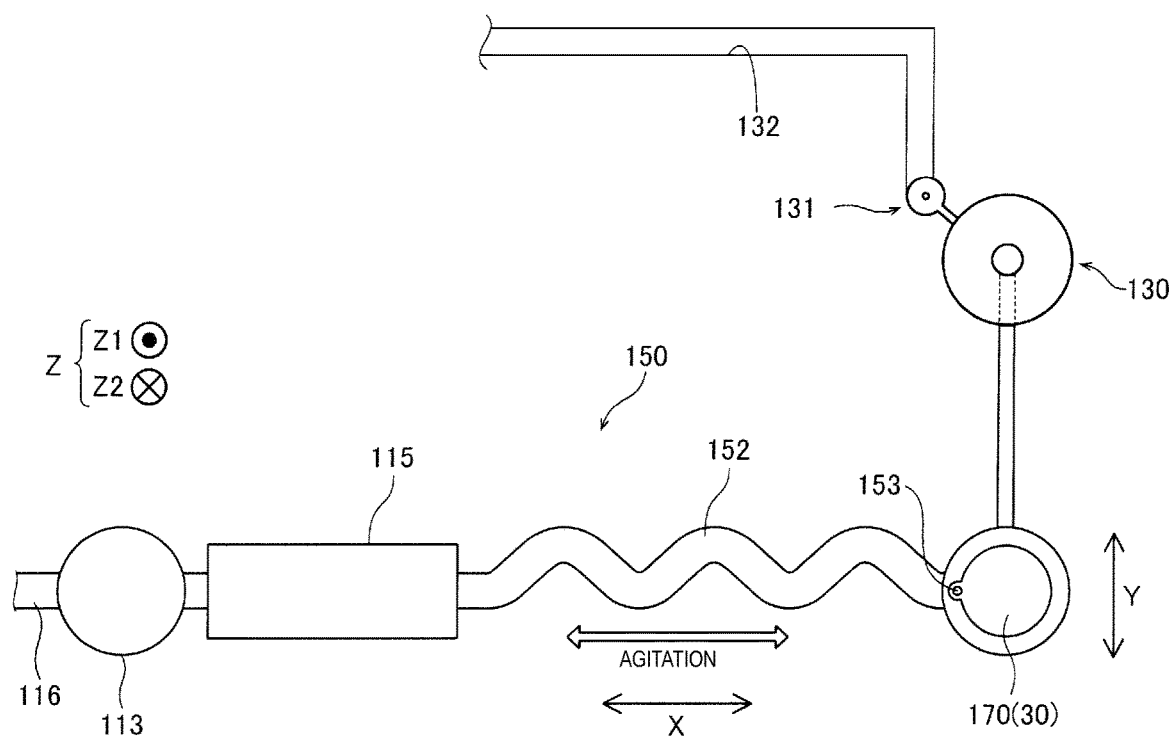
FIG. 25 is a fifth diagram illustrating another configuration example regarding the mixed liquid flow path.

As illustrated in FIG. 25, both ends of fourth liquid container 115 may be connected to passage part 116 and detection tank 170, and the mixed liquid may be discharged to detection tank 170 by the negative pressure from air chamber 130 connected to detection tank 170.

<R5 Flow Path>

Figure 26:
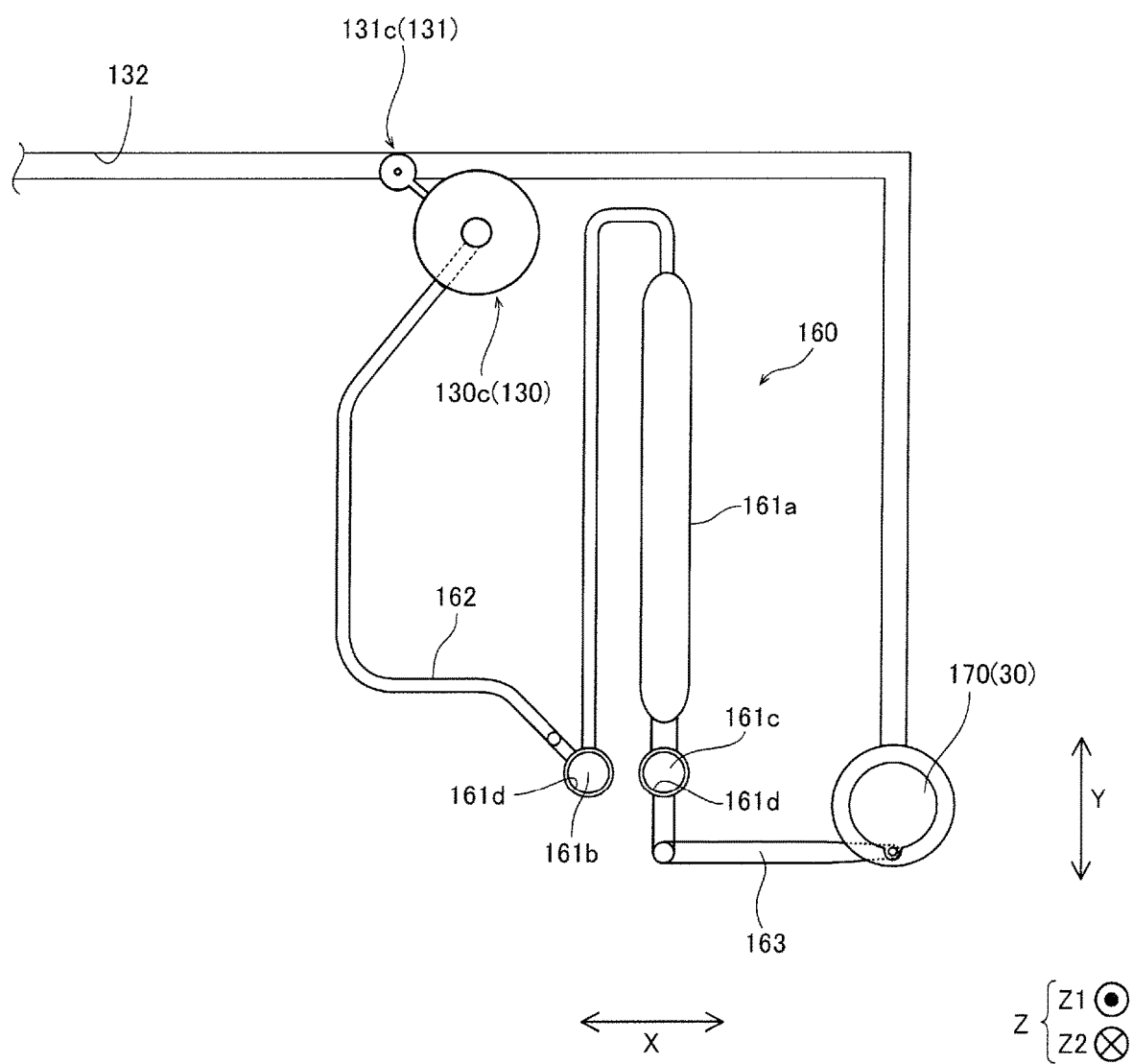
FIG. 26 is a schematic plan view illustrating a configuration example of an R5 flow path.

FIG. 26 illustrates a configuration example of R5 flow path 160. R5 flow path 160 includes, for example, R5 reagent tank 161, first portion 162, and second portion 163.

R5 reagent tank 161 has one end connected to air chamber 130*c* through first portion 162. R5 reagent tank 161 has the other end connected to detection tank 170 through second portion 163. R5 reagent tank 161 stores the R5 reagent. The R5 reagent is discharged to detection tank 170 by the air pressure in air chamber 130c.

As the configuration of R5 reagent tank 161, basically the same configuration as that of fourth liquid container 115 illustrated in FIG. 20 can be adopted. More specifically, R5 reagent tank 161 includes reagent storage portion 161a formed near the bottom of cartridge main body 100a. One side of reagent storage portion 161a is connected to first portion 162 through portion 161b extending in the thickness direction (Z direction) of cartridge main body 100a. The other side of reagent storage portion 161a is connected to second portion 163 through portion 161c extending in the Z direction. At an upper end of portion 161b, reduced diameter part 161d is formed. At an upper end of portion 161c, reduced diameter part 161e is formed.

Second portion 163 is connected to detection tank 170 from the back surface side of cartridge 100, for example. Thus, the R5 reagent can be discharged to detection tank 170 from below.

(Configuration of Detection Tank)

Figure 27:
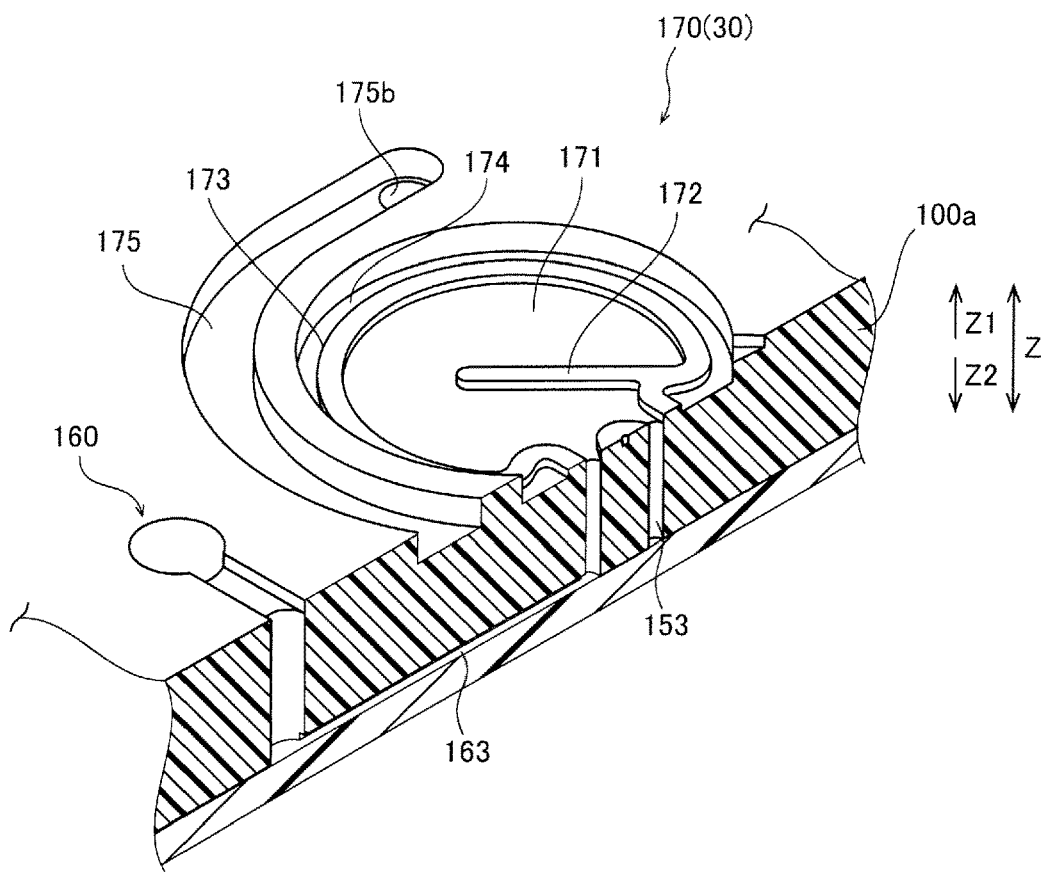
FIG. 27 is a schematic perspective cross-sectional view illustrating a configuration example of a detection tank.
Figure 28:
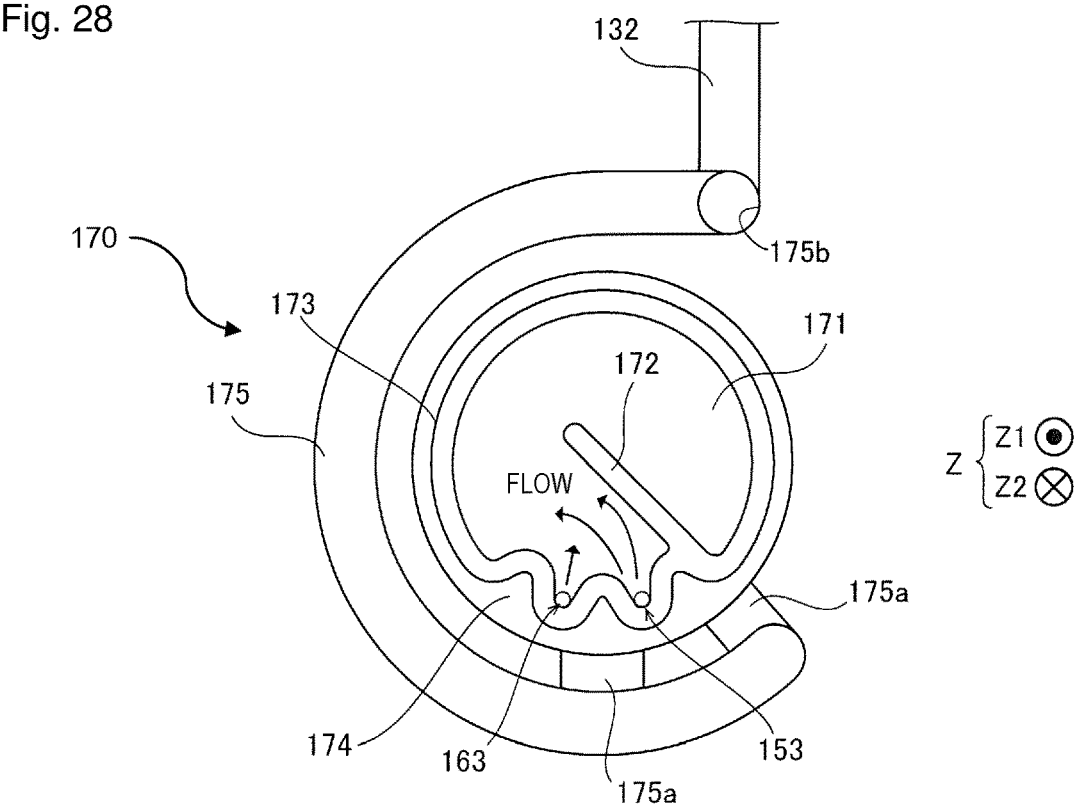
FIG. 28 is a schematic plan view illustrating a configuration example of the detection tank.

Detection tank 170 provides a measurement region for optical measurement of test substance 190 (complex 190c reacted with the R5 reagent). As illustrated in a configuration example of FIGS. 27 and 28, detection tank 170 includes, for example, liquid disposition part 171, flow control wall 172, step 173, external region 174, and air channel 175.

Liquid disposition part 171 is formed to be concave toward the back side from the front side surface of cartridge main body 100a. Liquid disposition part 171 accumulates the mixed liquid discharged from mixed liquid flow path 150 and the R5 reagent discharged from the R5 flow path 160. Detection tank 170 reacts labeled substance 193 in complex 190c contained in the mixed liquid with the substrate contained in the R5 reagent.

Flow control wall 172 protrudes from liquid disposition part 171. Flow control wall 172 is tilted toward the side where the exit of second portion 153 and exit of second portion 163 are arranged from the peripheral portion of liquid disposition part 171. Moreover, flow control wall 172 is linearly formed.

Step 173 is disposed along the periphery of liquid disposition part 171. Step 173 surrounds liquid disposition part 171. The mixed liquid added with the R5 reagent is accumulated in liquid disposition part 171 on the inside of step 173 in a planar view.

External region 174 is a region outside step 173. External region 174 is firmed into an arc shape in the planar view.

Air channel 175 is formed on the outside of external region 174. Air channel 175 is a groove formed in the front side surface of cartridge main body 100a. Air channel 175 is connected to liquid disposition part 171 through two connection parts 175a. Air channel 175 is connected to air flow path 132 through a hole 175b. Connection parts 175a are disposed near second portion 153 of mixed liquid flow path 150 and second portion 163 of R5 flow path 160.

When detection tank 170 is thus configured, air bubbles can escape through air channel 175 even if the air bubbles are discharged into liquid disposition part 171 after the liquid is discharged into liquid disposition part 171 from mixed liquid flow path 150 and R5 flow path 160.

[Configurations of Respective Parts in Sample Analyzer]

Figure 29:
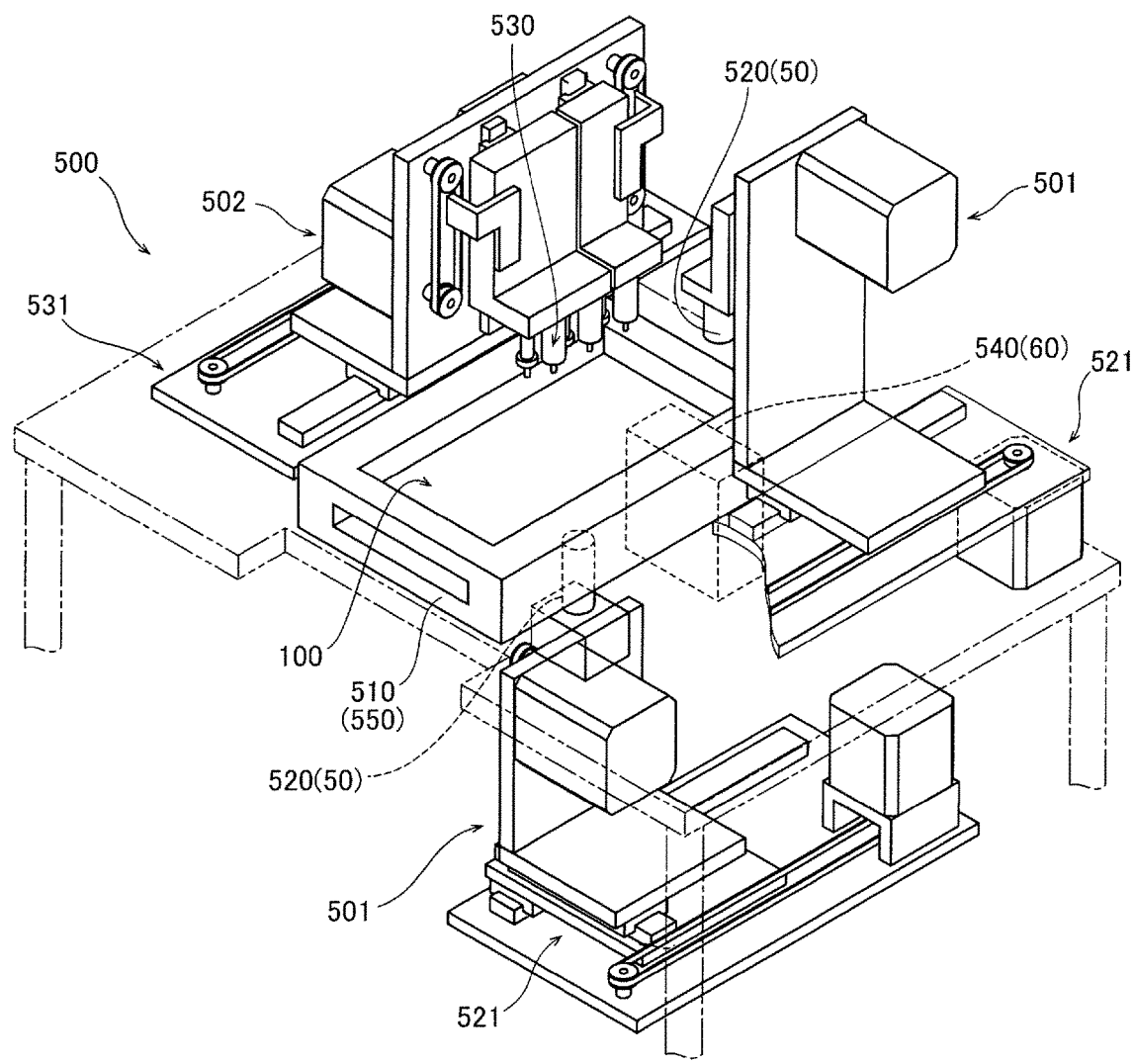
FIG. 29 is a schematic perspective view illustrating a configuration example of the respective parts in the sample analyzer.

Configurations of the respective parts in sample analyzer 500 are described. FIG. 29 illustrates a configuration example of sample analyzer 500. In the configuration example of FIG. 29, setting part 550 is integrated with heat block 510. Setting part 550 and heat block 510 may be separately provided.

Sample analysis cartridge 100 is held by heat block 510. In the configuration example of FIG. 29, magnet unit 501, plunger unit 502, and detector 540 are arranged on the sides of heat block 510.

Magnet unit 501 includes: permanent magnet 520 as magnetic source 50; and movement mechanism 521 configured to move permanent magnet 520 relative to sample analysis cartridge 100. Movement mechanism 521 can move permanent magnet 520 in a horizontal direction and in a vertical direction (cartridge thickness direction). When liquid containers 110, between which magnetic particles 191 are transported by the magnetic force, are linearly arranged, movement mechanism 521 may horizontally move only in one straight axial direction along the arrangement direction of respective liquid containers 110. Movement mechanism 521 enables the agitation operation illustrated in FIG. 16 by moving permanent magnet 520 in the vertical direction relative to liquid containers 110 in sample analysis cartridge 100 set in setting part 550.

When permanent magnets 520 are provided above and below sample analysis cartridge 100 set in setting part 550, two magnet units 501 are disposed. In this case, the horizontally moving structure of movement mechanism 521 may be shared by two magnet units 501. In this case, movement mechanism 521 enables the agitation operation illustrated in FIG. 16B by moving the permanent magnet 520 provided above the cartridge and permanent magnet 520 provided below the cartridge alternately close to the liquid containers 110 in sample analysis cartridge 100 set in setting part 550.

Plunger unit 502 includes, for example: plunger 530 configured to activate air chamber 130 and valve part 131; and movement mechanism 531 configured to move plunger 530 relative to sample analysis cartridge 100. Movement mechanism 531 can move plunger 530 in the vertical direction. When air chamber 130 and valve part 131 are linearly arranged, movement mechanism 531 may horizontally move only in one straight axial direction along the arrangement direction of air chamber 130 and valve part 131. When the same number of plungers 530 as those of air chambers 130 and valve parts 131 are provided, the horizontal positions of plungers 530 can be fixed. Thus, movement mechanism 531 may move only in the vertical direction.

Detector 540 is disposed at a position close to detection tank 170 in sample analysis cartridge 100. In FIG. 29, detector 540 is disposed at a position immediately below detection tank 170.

(Plunger)

In this embodiment, the liquid is transported by activating air chamber 130 in a closed state of valve part 131. Thus, plunger 530 for air chamber 130 and plunger 530 for valve part 131 may be configured so as to individually move up and down. As in a configuration example illustrated in FIG. 30, plungers 530 may be configured so as to move up and down all together. In such a case, the sample analyzer can be reduced in size by simplifying the mechanism for moving plungers 530 in the vertical direction.

Figure 30:
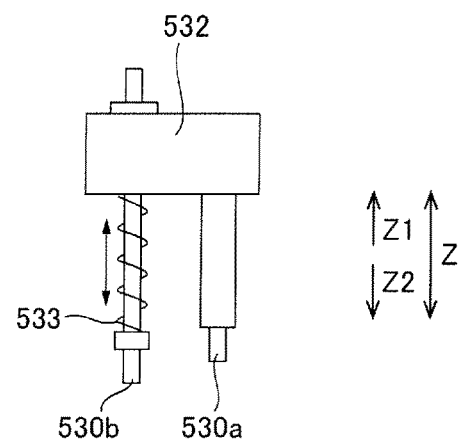
FIG. 30 is a schematic side view illustrating a configuration example of a plunger.

FIG. 30 illustrates the configuration example for activating air chamber 130 and valve part 131 all together. Plunger 530a is a plunger for activating air chamber 130, and plunger 530b is a plunger for opening and closing valve part 131. Respective plungers 530a and 530b are attached to holding block 532, and moved up and down all together by movement of holding block 532.

Plunger 530a is fixed to holding block 532. Plunger 530b is attached to holding block 532 in a state of being movable up and down relative to holding block 532. Plunger 530b is provided with energizing member 533 configured to energize plunger 530b in a downward direction protruding from holding block 532.

Thus, when holding block 532 is lowered toward sample analysis cartridge 100, plunger 530b first closes valve part 131. When holding block 532 is further lowered in this state, energizing member 533 is compressed and plunger 530b is moved relative to holding block 532. Thus, the position of plunger 530b can be maintained even if holding block 532 is moved. Therefore, by moving holding block 532 up and down in the closed state of valve part 131, plunger 530a can move the liquid back and forth within the flow path by moving up and down relative to air chamber 130. Moreover, by further lowering holding block 532, the liquid can be sent to the portion of supply destination from the flow path.

(Temperature Control in Cartridge)

In this embodiment, sample analyzer 500 controls the temperatures of the sample and reagent in sample analysis cartridge 100 to those required in the assay. Sample analyzer 500 uses heat block 510 to control the temperatures of the sample and reagent in sample analysis cartridge 100. Heat block 510 performs the temperature control using a heating wire or the like which generates heat with not-illustrated power supply, for example. When not only heating but also cooling is required, a thermoelectric element such as a Peltier element, for example, is used as heat block 510.

Figure 31:
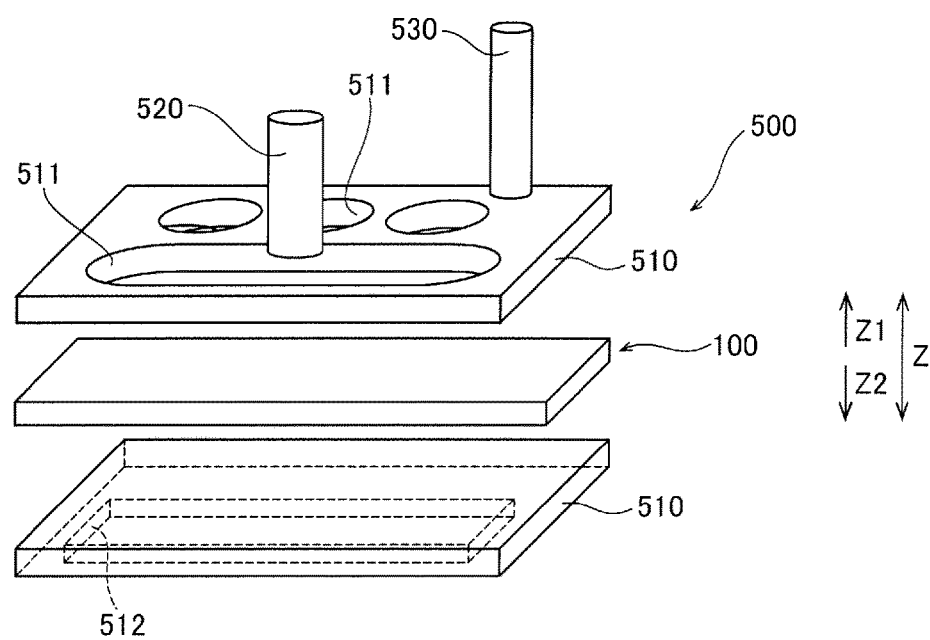
FIG. 31 is a schematic perspective view illustrating a configuration example of a heat block.

FIG. 31 illustrates a configuration example of the heat blocks according to this embodiment.

Heat blocks 510 are disposed on the upper and lower surfaces of sample analysis cartridge 100, for example. Heat block 510 may be disposed on any one of the upper and lower surfaces of sample analysis cartridge 100. In this embodiment, the upper surface of sample analysis cartridge 100 is a surface corresponding to the direction in which permanent magnet 520 for transporting magnetic particles 191 is disposed.

Heat block 510 disposed on the lower surface of sample analysis cartridge 100 is configured to cover at least a part of or all of a fluid structure associated with reaction. The fluid structure associated with reaction is the portion corresponding to sample flow path 140, liquid reaction part 112, second liquid container 114, mixed liquid flow path 150, R5 flow path 160, and the like, for example. Heat block 510 disposed on the lower surface may be configured to cover a fluid structure associated with the transportation of magnetic particles 191. The fluid structure associated with the transportation of magnetic particles 191 is the portion corresponding to first liquid container 111, liquid reaction part 112, third liquid container 113, second liquid container 114, fourth liquid container 115, passage part 116 provided between liquid containers 110 (see FIG. 4) in this embodiment. Heat block 510 disposed on the lower surface of sample analysis cartridge 100 may be configured to cover approximately the entire lower surface of sample analysis cartridge 100. The temperature control efficiency of sample analysis cartridge 100 is improved by heat block 510 covering approximately the entire lower surface of sample analysis cartridge 100.

Heat block 510 disposed on the upper surface of sample analysis cartridge 100 has holes 511 for plunger 530 and permanent magnet 520 to access sample analysis cartridge 100. Hole 511 for plunger 530 to access sample analysis cartridge 100 is provided at the position corresponding to air chamber 130 in sample analysis cartridge 100. Hole 511 for permanent magnet 520 to access sample analysis cartridge 100 is extended in the longitudinal direction of sample analysis cartridge 100. The hole extended in the longitudinal direction of sample analysis cartridge 100 enables permanent magnet 520 to be moved in the transportation direction of magnetic particles 191 while staying close to sample analysis cartridge 100.

As indicated by the broken lines in FIG. 31, a reduced thickness portion may be provided in heat block 510 on the lower surface of sample analysis cartridge 100. In FIG. 31, heat block 510 on the lower surface of sample analysis cartridge 100 has groove 512 extending in the longitudinal direction of sample analysis cartridge 100.

Sample analyzer 500 applies magnetic force to sample analysis cartridge 100 by inserting permanent magnet 520 provided on the lower surface of sample analysis cartridge 100 into groove 512. Groove 512 in heat block 510 does not penetrate heat block 510 from the lower surface to the upper surface. Thus, the magnetic force can be applied from the lower surface of sample analysis cartridge 100 without impairing the function to control the temperature on approximately the entire lower surface of sample analysis cartridge 100.

In Patent Document 1, the microchannels connecting the liquid containers containing the liquid are filled with the liquid. Thus, the movement of the magnetic particles makes it likely for the liquid in the liquid container to be mixed into the liquid in the liquid container adjacent thereto. As a result, analysis precision for the test substance may be reduced.

The embodiments described above suppresses the mixing of a liquid in a liquid container into a liquid in a liquid container adjacent thereto by movement of magnetic particles in sample measurement using a sample analysis cartridge.

Note that the embodiment disclosed herein is merely illustrative in all aspects and should not be recognized as being restrictive. The scope of the invention is defined by the scope of the claims rather than by the above description of the embodiment, and is intended to include the meaning equivalent to the scope of the claims and all modifications within the scope.

The invention claimed is:

1. A method of detecting a test substance contained in a sample, comprising:
   applying a sample to a cartridge comprising:
      at least first and second chambers filled with liquid-based first and second reagents, respectively; and
      a passage adjacent to an upper surface of the cartridge and connecting the first and second chambers with a gas-phase space, wherein openings are formed in upper parts of the first and second chambers, the first and second chambers are connected through the respective openings by the passage, the passage is provided above the first and second chambers and covered with a cover part, and the first and second chambers are filled with the first and second reagents up to the cover part so that a first liquid phase formed by the first reagent and a second liquid phase formed by the second reagent are separated with the gas-phase space in the passage;
   transferring at least a part of the sample to the first chamber so that magnetic particles contained in the first reagent react with a test substance in the sample, the magnetic particles carrying the test substance in response to the magnetic particles reacting with the test substance;

attracting, in the first liquid phase of the first reagent, the magnetic particles close to the cover part with a magnetic source;

transferring, by moving the magnetic source along the cover part, a complex of the test substance and the magnetic particles from the first liquid phase to the second liquid phase through the gas-phase space so that the complex reacts with a labeled substance contained in the second reagent; and detecting the test substance in the complex based on the labeled substance.

2. The method of detecting a test substance, according to claim 1, wherein
the magnetic particles are moved in a vertical direction within the first chamber by moving the magnetic source.

3. The method of detecting a test substance, according to claim 1, wherein
the cartridge further includes a liquid reaction part in which a reaction of the magnetic particles with the test substance takes place, and
the magnetic particles are transported from the first chamber to the liquid reaction part through the gas-phase space of the passage.

4. The method of detecting a test substance, according to claim 3, wherein
the cartridge further comprises a sample flow path connected to the liquid reaction part, and
a mixture of the first reagent and the sample containing the test substance is agitated by an air pressure inside the sample flow path, and the mixture is discharged to the liquid reaction part.

5. The method of detecting a test substance, according to claim 1, wherein
the cartridge further comprises a third chamber that is located between the first and second chambers and contains a cleaning liquid, and
unwanted substances attached to the magnetic particles are dispersed into the cleaning liquid by transporting the magnetic particles coupled to the test substance to the third chamber through the gas-phase space of the passage.

6. The method of detecting a test substance, according to claim 1, wherein
the cartridge further comprises a third chamber containing a cleaning liquid, and
the complex of the test substance and the labeled substance is carried by the magnetic particles by transporting the magnetic particles coupled to the test substance from the third chamber to the second chamber adjacent thereto through the gas-phase space of the passage.

7. The method of detecting a test substance, according to claim 6, wherein
the magnetic particles are sequentially transported to the third chamber on an upstream side, the second chamber, and the third chamber on a downstream side in the recited order through the gas-phase space of the passage.

8. The method of detecting a test substance, according to claim 1, wherein
the cartridge further comprises a fourth chamber that contains a buffer liquid, and
the magnetic particles carrying the complex of the test substance and the labeled substance are dispersed into the buffer liquid by transporting the magnetic particles carrying the complex to the fourth chamber through the gas-phase space of the passage.

9. The method of detecting a test substance, according to claim 8, wherein
the cartridge further includes a detection tank in which a reaction of the labeled substance with a substrate takes place, and
a mixed liquid of the complex and the buffer liquid in the fourth chamber is transported to the detection tank through a mixed liquid flow path.

10. The method of detecting a test substance, according to claim 1, wherein
an area of a bottom inner surface of each of the first and second chambers is larger than an opening area of the openings that connect each of the first and second chambers to the passage.

11. A method of detecting a test substance contained in a sample by use of a cartridge, comprising:
receiving a sample with the cartridge;
transferring at least a part of the sample to a first chamber, of the cartridge, which accommodates a liquid-based first reagent filled up to a cover part, so that magnetic particles contained in the first reagent react with a test substance in the sample, the magnetic particles carrying the test substance in response to the magnetic particles reacting with the test substance;
attracting, in a first liquid phase formed by the first reagent, the magnetic particles close to the cover part with a magnetic source;
transferring, by moving the magnetic source along the cover part, a complex of the test substance and the magnetic particles from the first liquid phase to a second liquid phase formed by a second liquid-based reagent through a gas phase defined by a passage connecting the first chamber and a second chamber, of the cartridge, which accommodates the second reagent filled up to the cover part, so that the complex reacts with a labeled substance contained in the second reagent, wherein the passage is provided adjacent to an upper surface of the cartridge and wherein openings are formed in upper parts of the first and second chambers, and the first and second chambers are connected through the respective openings by the passage, and wherein the passage is provided above the first and second chambers and covered with the cover part so that the first reagent and the second reagent filled up to the cover part are separated with the gas-phase in the passage; and
detecting the test substance in the complex based on the labeled substance.

* * * * *